US007820833B2

(12) United States Patent
Sem et al.

(10) Patent No.: US 7,820,833 B2
(45) Date of Patent: Oct. 26, 2010

(54) DITHIO COMPOUNDS

(75) Inventors: Daniel S. Sem, New Berlin, WI (US); Phani Kumar Pullela, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 1092 days.

(21) Appl. No.: 11/512,485

(22) Filed: Aug. 30, 2006

(65) Prior Publication Data

US 2007/0054410 A1 Mar. 8, 2007

Related U.S. Application Data

(60) Provisional application No. 60/715,114, filed on Sep. 8, 2005.

(51) Int. Cl.
*C07D 311/90* (2006.01)
*C07D 311/14* (2006.01)
*C07D 335/20* (2006.01)
*C07D 311/82* (2006.01)

(52) U.S. Cl. .................. 549/223; 549/27; 549/288; 549/388; 549/394

(58) Field of Classification Search .................. 549/223, 549/227, 27, 288, 388, 394
See application file for complete search history.

(56) References Cited

U.S. PATENT DOCUMENTS 7,585,643 B2    9/2009    Sem
2009/0325179 A1    12/2009    Sem

OTHER PUBLICATIONS

Yamani et al, Tetrahedron, vol. 55 p. 9143-9150 (1999).*
Taurai Chiku, Phani Kumar Pullela, and Daniel S. Sem, "A Dithio-Coupled Kinase and ATPase Assay", Journal of Biomolecular Screening 11(X); 2006 pp. 1-10 (galley copy not yet published).
Cohen, Philip, "The Origins of Protein Phosphorylation", Nature Cell Biology, vol. 4, May 2002, pp. E127-E130.
Cohen, Philip, "The Role of Protein Phosphorylation in Human Health and Disease", The Sir Hans Krebs Medal Lecture, Delivered on Jun. 30, 2001 at the FEBS Meeting in Lisbon, MRC Protein Phosphorylation Unit, School of Life Sciences, University of Dundee, Scotland; Eur. J. Biochem 268, pp. 5001-5010 (2001).
Hanks, Steven K. and Hunter, Tony, "The Eukaryotic Protein Kinase Superfamily: Kinase (Catalytic) Domain Structure and Classification", Protein Kinases 6, The FASEB Journal, vol. 9, May 1995, pp. 576-596.
Marras, Salvatore A. E., Kramer, Fred Russell, and Tyagi, Sanjay, "Efficiencies of Fluorescence Resonance Energy Transfer and Contact-Mediated Quenching in Oligonucleotide Probes", Nucleic Acids Research, 2002, vol. 30, No. 21, e122, pp. 1-8.
Nick, Jerry A. et al, "Role of p38 Mitogen-Activated Protein Kinase in a Murine Model of Pulmonary Inflammation", The Journal of Immunology, 2000, 164: pp. 2151-2159.
Zaman, G. J. R., Garritsen, A., De Boer, TH., and Van Boeckel C. A. A., "Fluorescence Assays for High-Throughput Screening of Protein Kinases", Combinatorial Chemistry & High Throughput Screening, 2003, vol. 6, No. 4, pp. 313-320.
Xia, Wensheng et al, "Applications of Fluorescent Polymer Superquenching to High Throughput Screening Assays for Protein Kinases", Assay and Drug Development Technologies, vol. 2, No. 2, 2004, pp. 183-192.
Blume-Jensen, Peter and Hunter, Tony, "Oncogenic Kinase Signalling", Nature, vol. 411, May 17, 2001, pp. 355-365.
Manning, G., Whyte, D. B., Martinez, R., Hunter, T., and Sudarsanam, S., "The Protein Kinase Complement of the Human Genome", Science, Dec. 6, 2002, vol. 298, pp. 1912-1916, 1933-1934.
Daly, Thomas J., Olson, John S., and Matthews, Kathleen Shive, "Formation of Mixed Disulfide Adducts at Cysteine-281 of the Lactose Repressor Protein Affects Operator and Inducer Binding Parameters", Biochemistry, 1986, vol. 25, pp. 5468-5474.
Ways, D. Kirk, and Sheetz, Matthew J., "The Role of Protein Kinase C in the Development of the Complications of Diabetes", Vitamins and Hormones, vol. 60, pp. 149-193, Copyright © 2001.
Eckstein, Fritz and Goody, Roger S., "Synthesis and Properties of Diastereoisomers of Adenosine 5'-(O-1-Thiotriphosphate) and Adenosine 5'-(O-2-Thiotriphosphate)" Biochemistry, vol. 15, No. 8, 1976, pp. 1685-1691.
Viola, Ronald E., Raushel, Frank M., Rendina, Alan R., and Cleland, W. W., "Substrate Synergism and the Kinetic Mechanism of Yeast Hexokinase", Biochemistry, 1982, vol. 21, pp. 1295-1302.
Pullela, Phani Kumar, Chiku, Taurai, and Sem, Daniel S., "Fluorescence Probes with Utility in Kinase Assay and Redox Sensing", The FASEB Journal, Mar. 4, 2005, vol. 19, No. 4, Experimental Biology/IUPS 2005: Meeting Abstracts, p. A265.
Invitrogen Product Description for BODIPY® FL L-cystine available at least as early as Jan. 1, 2003.
Chiku, Taurai, Pullela, Phani Kumar, and Sem, Daniel S., "A Dithio-Coupled Kinase and ATPase Assay", Journal of Biomolecular Screening (X)X; 2006, pp. 1-10.
Chiku, Taurai, Pullela, Phani Kumar, and Sem, Daniel S., "A General Dithiol-Coupled UV Vis and Fluorescence Assay for Kinases", FASEB Journal, 19 (4, Part 1 Suppl.) A265-266, Abstract 212.4, 2005.
Churchich, Jorge E. and Wu, Christine, "Nucleoside Phosphorothioates As Probes of the Nucleotide Binding Site of Brain Pyridoxal Kinase", The Journal of Biological Chemistry, vol. 257, No. 20, Oct. 25, 1982, pp. 12136-12140.
Kupcho, Kevin, Somberg, Richard, Bulleit, Bob, and Goueli, Said A., "A Homogeneous, Nonradioactive High-Throughput Fluorogenic Protein Kinase Assay", Analytical Biochemistry, 317 (2003) pp. 210-217.

(Continued)

*Primary Examiner*—Bernard Dentz
(74) *Attorney, Agent, or Firm*—Andrus, Sceales, Starke & Sawall, LLP

(57) ABSTRACT

Disclosed herein are dithio compounds that include at least one fluorophore. The compounds additionally may include a different fluorophore or a non-fluorophore. The dithio compounds may be used as reagents for detecting thiol-containing compounds.

25 Claims, 18 Drawing Sheets

OTHER PUBLICATIONS

Pullela, Phani Kumar, Chiku, Taurai, Carvan, Michael J. (III), and Sem, Daniel S., "Fluorescence-Based Detection of Thiols in Vitro and in Vivo Using Dithiol Probes", Analytical Biochemistry, 352 (2006) pp. 265-273.

Mikula, Ivan, Demeler, Borries, and Martasek, Pavel, "Study of the Oligomeric Status of Coproporphyrinogen Oxidase (CPO) Using Analytical Ultracentrifugation (AU)", The FASEB Journal, Mar. 4, 2005, vol. 19, No. 4, Experimental Biology/IUPS 2005: Meeting Abstracts, p. A265.

* cited by examiner

Figure 1. pH-dependent behavior of fluorophores

Figure 2. Synthesis of dithio compounds

Figure 3. Synthesis of the dithio compound F-DAPS-R

Figure 4. Structure of F-DAPS-R at acidic ph (a); basic pH (b); and emission at different pH's (c)

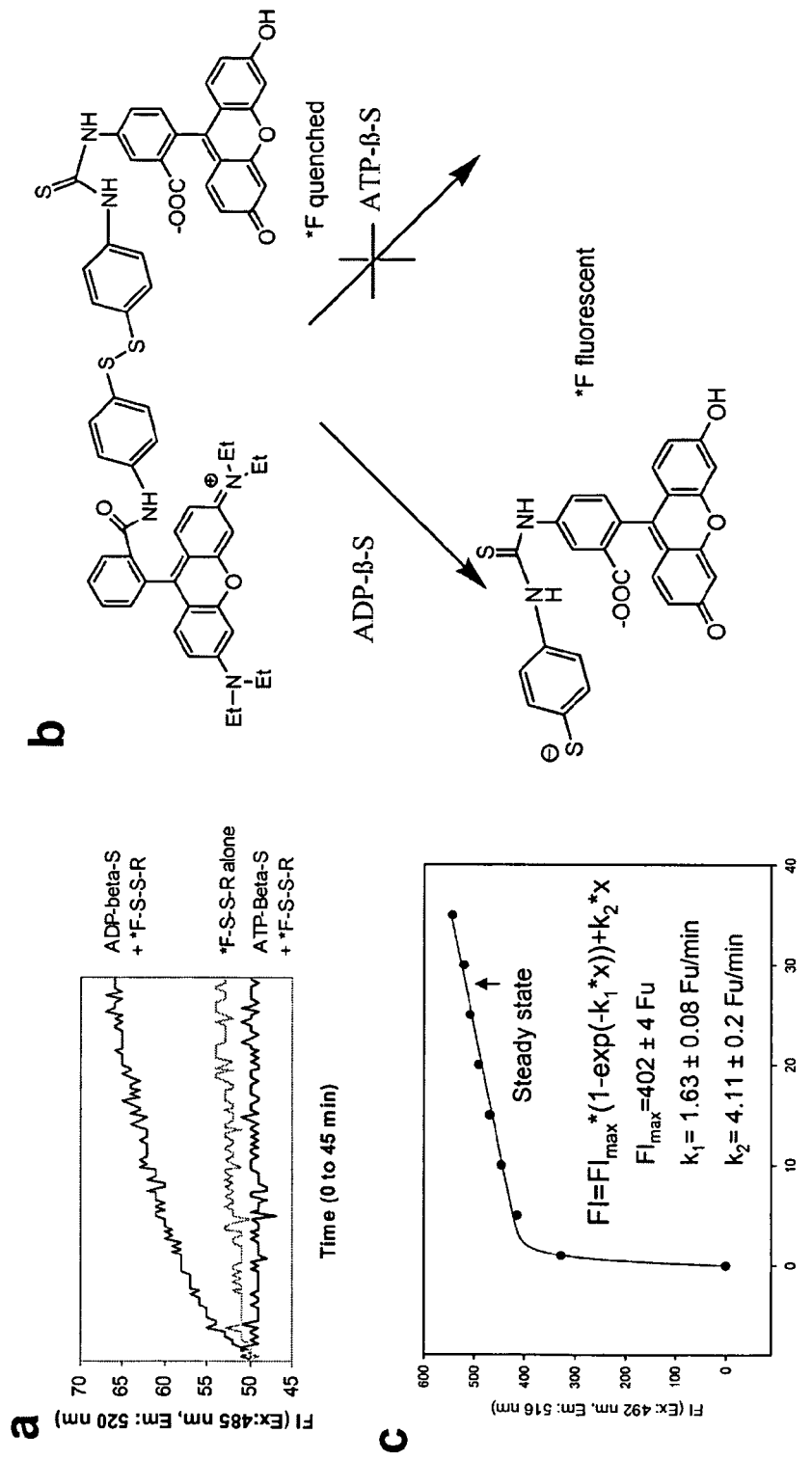
Figure 12. Selective detection of ADPβS versus ATPβS

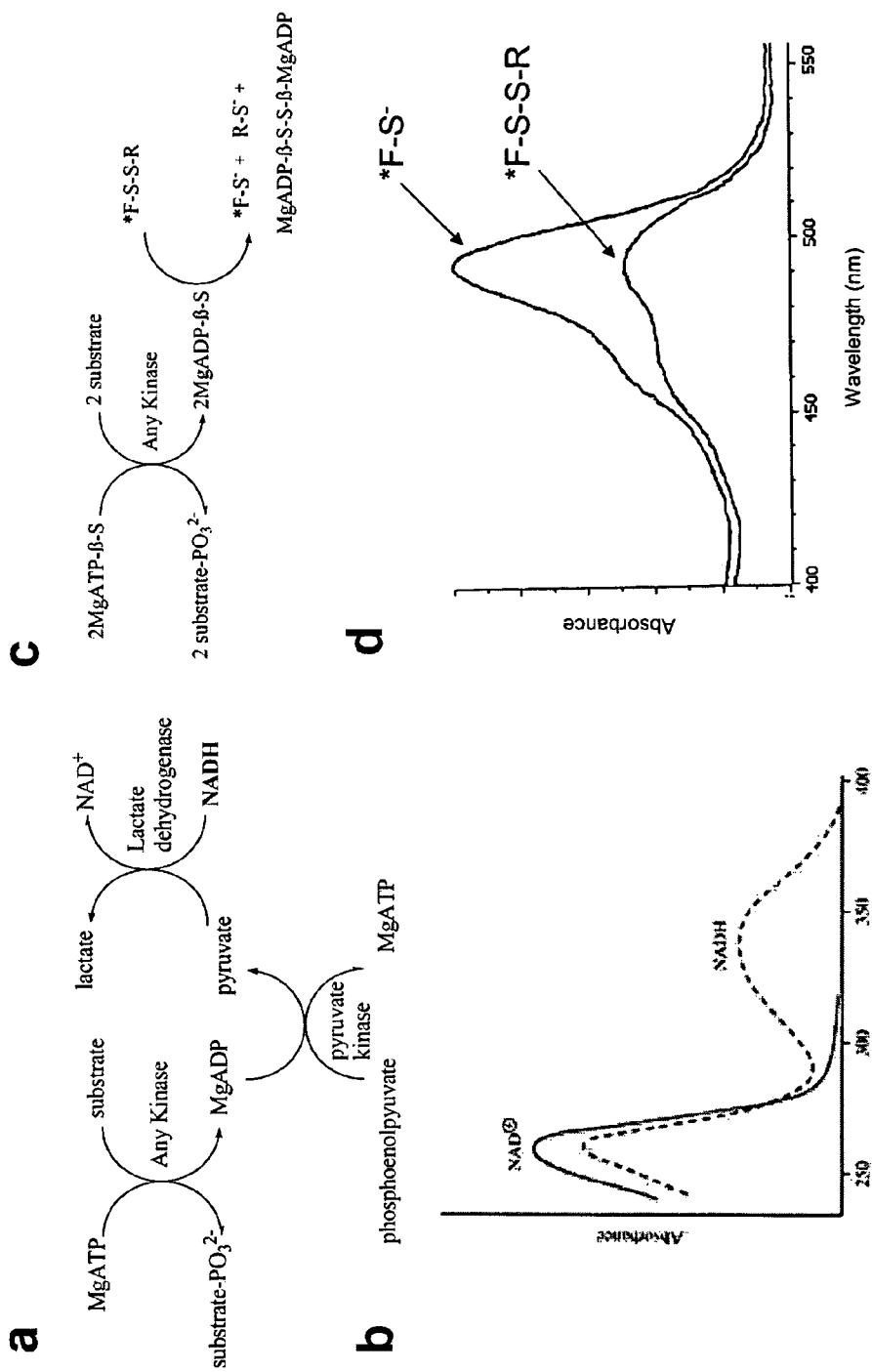
Figure 13. Common coupled kinase assay versus thiol-based F-DAPS-R coupled assay

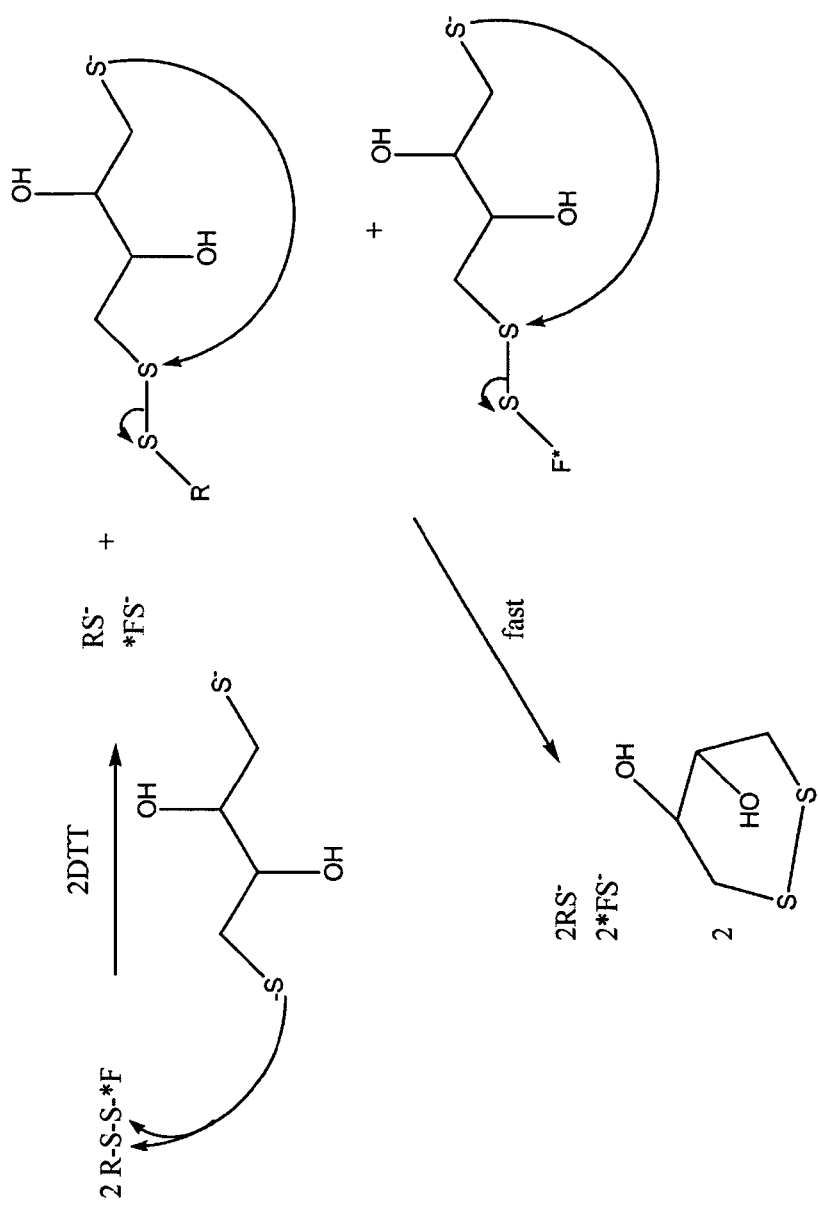
Figure 14. Proposed mechanism for reaction of DTT with F-S-S-R dithio reagent

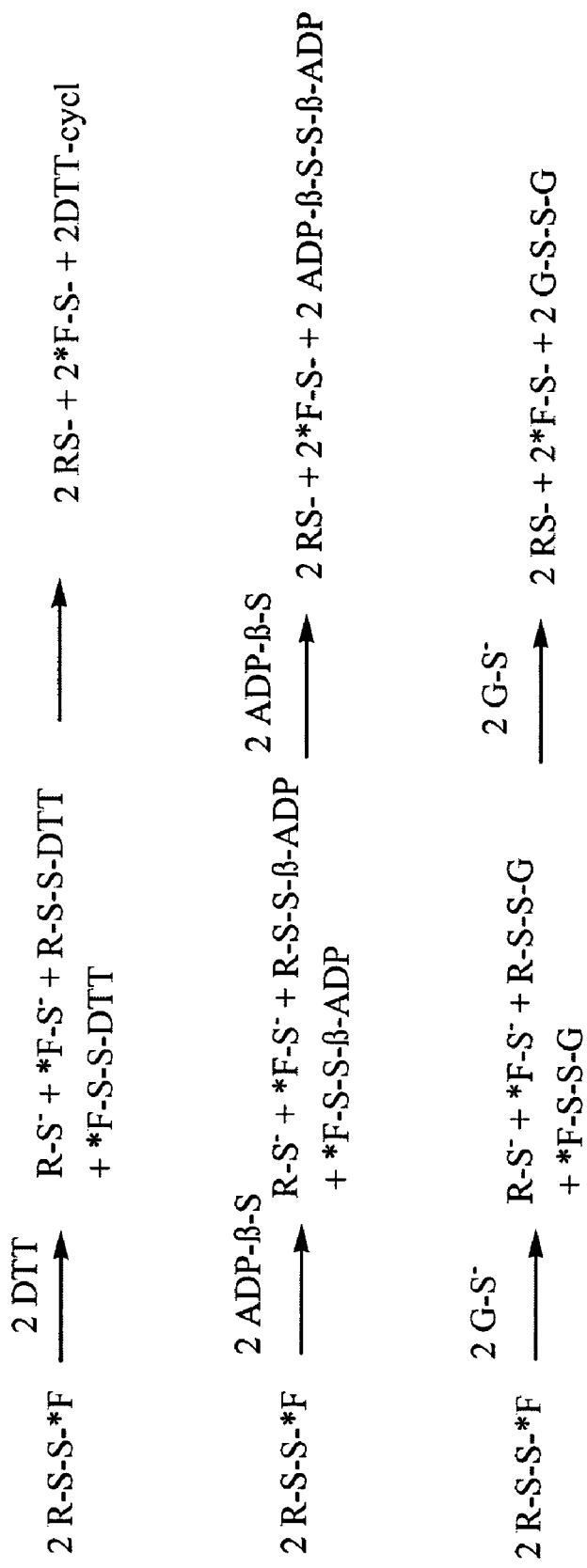
Figure 15. Reaction of fluorescein/rhodamine diamino phenyl disulfide reagent (F-DAPS-R) with selected thiols

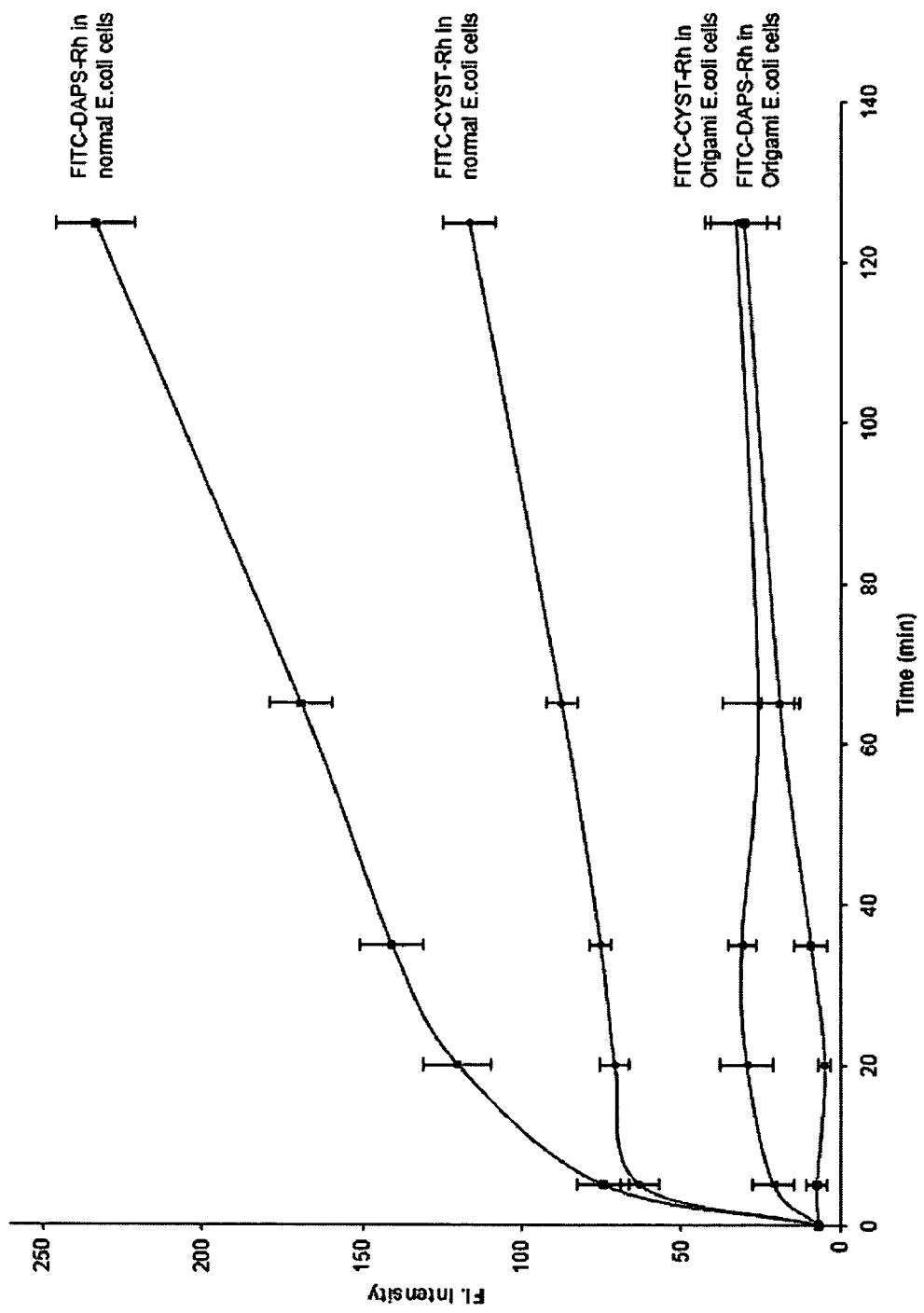
Figures 16. Uptake of F-S-S-R reagents into normal E. coli cells (top two curves) using a reagent that includes an aliphatic linker (FITC-CYST-Rh) or an aromatic linker (FITC-DAPS-Rh).

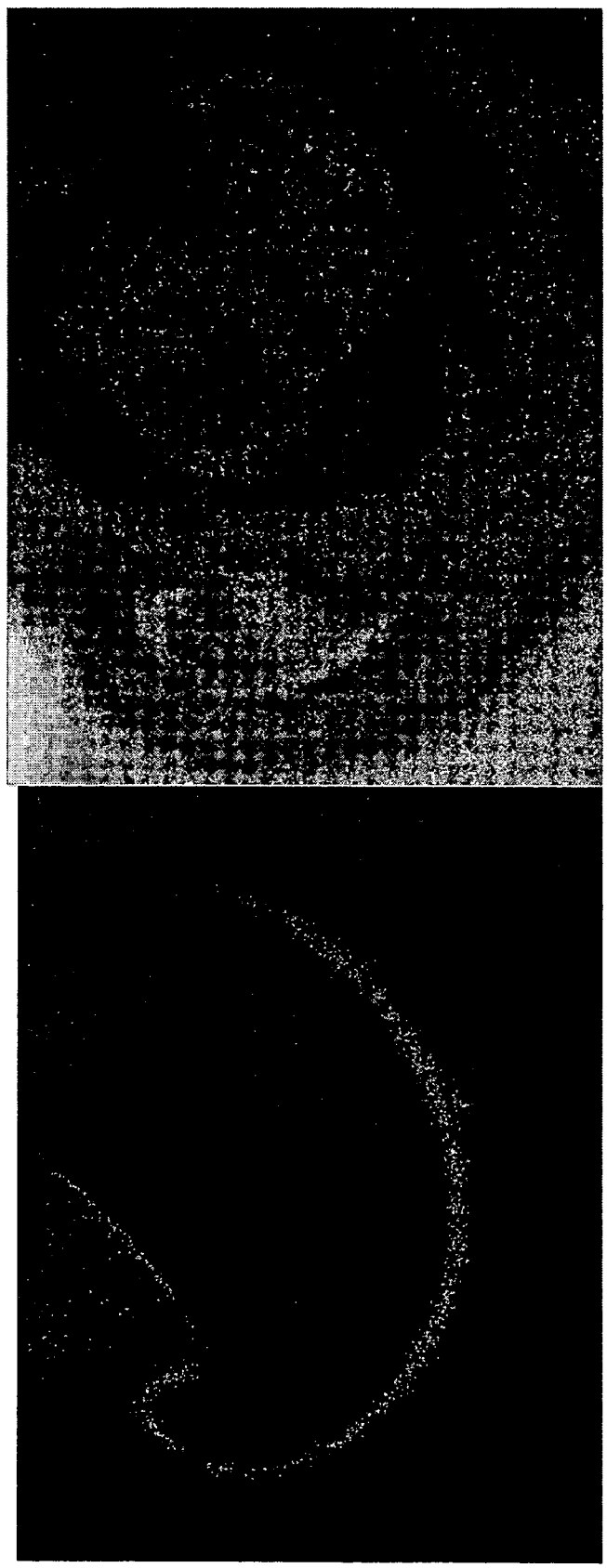
Figure 17. Exposure of zebrafish embryo at 1 dpf to F-DAPS-R probe: Left, fluorescence image (Ex@489 nm); Right, corresponding bright-field image

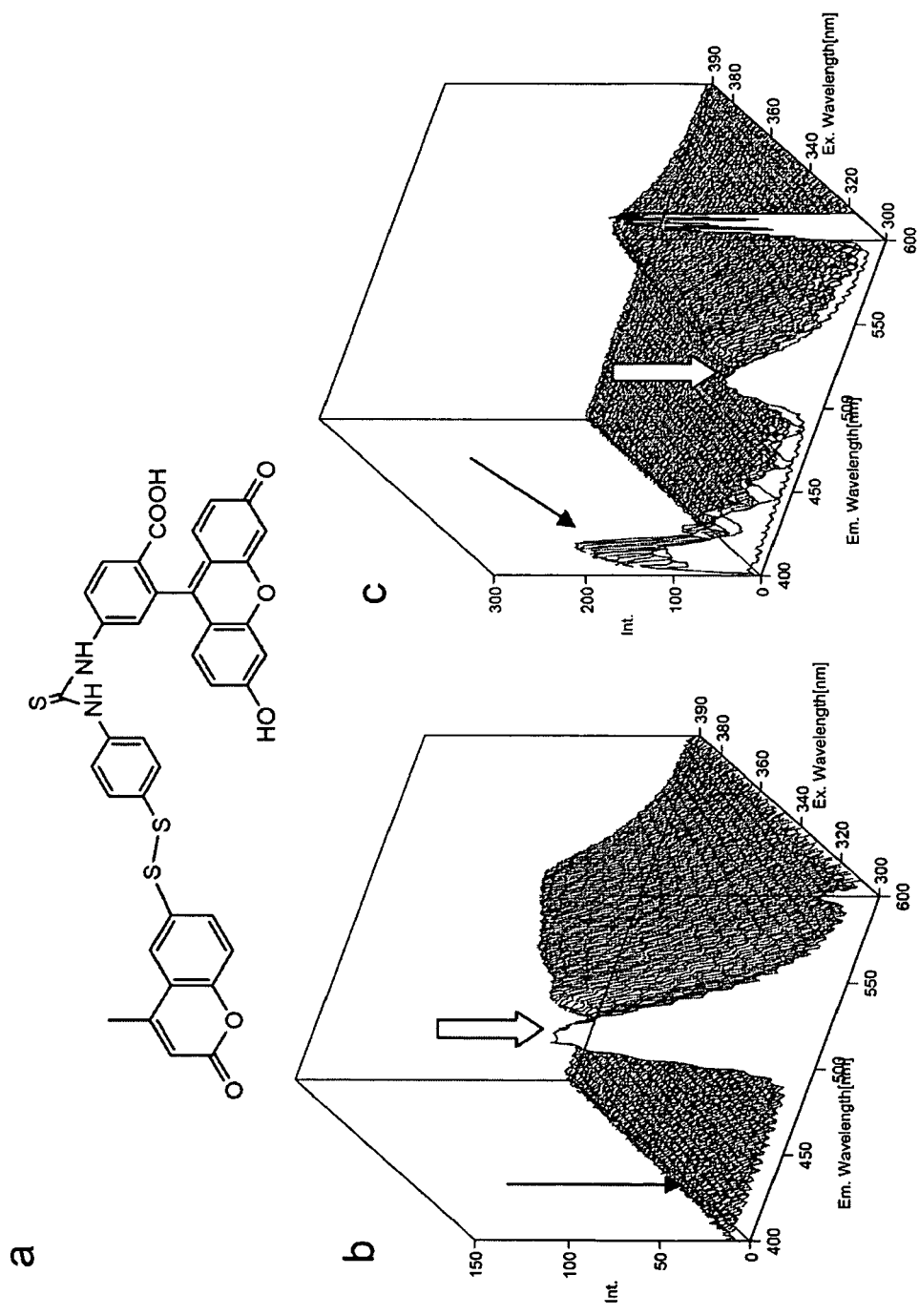
Figure 18. FRET-based detection of thiols

DITHIO COMPOUNDS

CROSS-REFERENCE TO RELATED APPLICATIONS

The present application claims the benefit under 35 U.S.C. §119(e) to U.S. Provisional Application No. 60/715,114, filed on Sep. 8, 2005, the entire contents of which are incorporated herein by reference.

BACKGROUND

The disclosed compounds generally relate to the field of dithio reagents. In particular, the disclosed compounds generally relate to fluorescent dithio reagents that are useful for detecting thiol-containing compounds.

Thiols are ubiquitous in cellular biochemistry, playing important roles in determining protein structure (as disulfide linkages) and enzymatic mechanisms (as covalent catalysts). Furthermore, the redox state in the cell is largely regulated by the thiol/disulfide status of glutathione in the cell (i.e., GSH vs GSSG). In addition, reduced glutathione (i.e., the thiol form or GSH) also plays a control role in drug metabolism by attacking electrophilic atoms. Therefore, thiol detection and quantitation is important in cellular biochemistry, and to date has been accomplished most commonly by performing UV-Visible assays using calorimetric reagents such as Ellman's reagent.

Fluorescence detection systems (e.g., fluorescence spectroscopy) have been widely used to study the structure, mechanism and function of different proteins and enzymes, and especially in enzymatic activity or binding assays. Fluorescence detection systems are useful in that they generally have high sensitivity and a good dynamic range for detection. In addition, many generic fluorescent reagents are available, as well as commercially available equipment for detecting particular reagents. Fluorescence detection systems may be amenable to high throughput screening (e.g., using any bench-top fluorescence plate reader). Potential drawbacks associated with some fluorescence reagents may include photobleaching, stability, and purity of the utilized fluorophore. Some commercially available fluorescent labeling reagents are mixtures of isomers or have high photobleaching or cause uncontrolled labeling, which prevents them from giving reliable and reproducible results.

As such, fluorescent dithio reagents are desirable. In particular, fluorescent dithio reagents that are photostable, single isomers are desirable.

SUMMARY

Disclosed herein are dithio compounds. The dithio compounds described herein may be used in methods for detecting thiol-containing compounds.

The dithio compounds may have a formula D-S—S-A, where "D" includes a donor fluorophore and "A" includes an acceptor fluorophore. In some embodiments, the acceptor fluorophore is different from the donor fluorophore and is capable of at least one of: (a) quenching the donor fluorophore; (b) increasing or decreasing an extinction coefficient of the donor fluorophore; and (c) sensitized emission when excited by the donor fluorophore. The donor fluorophore may have a maximum absorbance ($Abs_{max}$) for light of a particular wavelength ($\lambda$) that differs from the $Abs_{max}$ of the acceptor fluorophore. For example, the acceptor fluorophore and the donor fluorophore may have maximum absorbances for light having wavelengths that differ by at least about 10 nm, preferably 15 nm, more preferably 20 nm, and even more preferably 25 nm. The donor fluorophore may have a maximum emission ($Em_{max}$) for light of particular wavelength that differs from the $Em_{max}$ of the acceptor fluorophore. For example, the acceptor fluorophore and the donor fluorophore may have maximum emissions for light having wavelengths that differ by at least about 10 nm, preferably 15 nm, more preferably 20 nm, and even more preferably 25 nm.

In some embodiments, the donor fluorophore has an emission spectrum and the acceptor fluorophore has an absorption spectrum, such that the emission spectrum and absorption spectrum overlap. In particular, the emission spectrum and the absorption spectrum may overlap by about 20-100%, preferably about 40-100%, more preferably about 60-100%, and even more preferably about 70-100%.

The dithio compounds may include a donor fluorophore and an acceptor fluorophore such that the acceptor fluorophore is capable of quenching the donor fluorophore. In some embodiments, the acceptor fluorophore is capable of quenching the donor fluorophore by dynamic quenching. The acceptor fluorophore may be capable of quenching the donor fluorophore by dynamic quenching that occurs by fluorescence resonance energy transfer ("FRET"). The acceptor fluorophore may be capable of quenching the donor fluorophore by static quenching.

In some embodiments, the dithio compounds may include a donor fluorophore and an acceptor fluorophore such that the donor fluorophore is capable of inducing sensitized emission in the acceptor fluorophore. In some embodiments, the acceptor fluorophore may be capable of inducing sensitized emission by FRET.

The dithio compounds may include a donor fluorophore and an acceptor fluorophore that are present at a selected distance within the compounds. For example, the donor fluorophore and the acceptor fluorophore may be present in the dithio compounds at a distance of about 6-100 angstroms, preferably 15-75 angstroms, more preferably about 30-70 angstroms. In some embodiments, the donor fluorophore and the acceptor fluorophore may be present in the dithio compounds at a distance of about 3-100 angstroms, preferably 3-75 angstroms, more preferably about 3-50 angstroms. The donor fluorophore and the acceptor fluorophore may be present in the dithio compounds at a distance that is suitable to permit FRET. In some embodiments, the donor fluorophore and the acceptor fluorophore are present in the compound at a distance of no more than about 20 angstroms.

The dithio compounds may include any suitable donor fluorophore and any suitable acceptor fluorophore. For example, suitable donor fluorophores and suitable acceptor fluorophores include xanthene-type fluorophores such as fluorescein-type fluorophores and rhodamine-type fluorophores.

The dithio compounds may include a donor fluorophore selected from a group consisting of fluorescein-type fluorophores, rhodamine-type fluorophores, xanthine-type fluorophores, naphthalene-type fluorophores, carbocyanine-type fluorophores, dipyrromethene boron-type fluorophores, coumarin-type fluorophores, acridine-type fluorophores, pyrene-type fluorophores, DANSYL-type fluorophores, and lanthanide chelate-type fluorophores. The dithio compounds may include an acceptor fluorophore selected from the group consisting of fluorescein-type fluorophores, rhodamine-type fluorophores, naphthalene-type fluorophores, coumarin-type fluorophores, and DANSYL-type fluorophores. Suitable fluorophores may include lanthanide chelates.

In suitable embodiments, the dithio compounds include a fluorescein-type fluorophore as a donor fluorophore and a rhodamine-type fluorophore as an acceptor fluorophore. The fluorescein-type fluorophore and the rhodamine-type fluorophore may be present in the dithio compounds at a selected distance, (e.g., about 40-60 angstroms or about 10-60 angstroms).

In suitable embodiments, the dithio compounds include a naphthalene-type fluorophore as a donor fluorophore and a fluorescein-type fluorophore as an acceptor fluorophore. The naphthalene-type fluorophore and the fluorescein-type fluorophore may be present in the compounds at a selected distance, (e.g., about 40-60 angstroms or about 10-60 angstroms).

In suitable embodiments, the dithio compounds include a DANSYL-type fluorophore as a donor fluorophore and a fluorescein-type fluorophore as an acceptor fluorophore. The DANSYL-type fluorophore and the fluorescein-type fluorophore may be present in the dithio compound at a selected distance, (e.g., about 10-50 angstroms or about 25-45 angstroms).

Also disclosed are methods for preparing dithio compounds by reacting precursors, the dithio compounds having a formula D-S—S-A, in which "D" includes a donor fluorophore and "A" includes an acceptor fluorophore. The methods include reacting precursors that include: (A) a first precursor that includes a donor fluorophore; (B) a second precursor that includes an acceptor fluorophore; and (C) a dithio reagent. The dithio reagent typically has a formula $X^1$—S—S—$X^2$, where $X^1$ and $X^2$ may be the same or different and each includes at least one reactive group capable of reacting with the first precursor and the second precursor. In some embodiments, the precursors for preparing the dithio compounds include: (A) a first precursor including a fluorescein-type fluorophore; (B) a second precursor including a rhodamine-type fluorophore; and (C) a dithio reagent having the formula $X^1$—S—S—$X^2$, where $X^1$ and $X^2$ may be the same or different and each include at least one reactive group capable of reacting with the first precursor and the second precursor. In other embodiments, the precursors for preparing the dithio compounds include: (A) a first precursor including a naphthalene-type fluorophore; (B) a second precursor including a rhodamine-type fluorophore; and (C) a dithio reagent having the formula $X^1$—S—S—$X^2$, where $X^1$ and $X^2$ may be the same or different and each include at least one reactive group capable of reacting with the first precursor and the second precursor. In further embodiments, the precursors for preparing the dithio compounds include: (A) a first precursor including a DANSYL-type fluorophore; (B) a second precursor including a fluorescein-type fluorophore; and (C) a dithio reagent having the formula $X^1$—S—S—$X^2$, where $X^1$ and $X^2$ may be the same or different and each include at least one reactive group capable of reacting with the first precursor and the second precursor.

In suitable embodiments of the method for preparing dithio compounds, the first precursor may include a donor fluorophore selected from the group consisting of fluorescein-type fluorophores, rhodamine-type fluorophores, xanthine-type fluorophores, naphthalene-type fluorophores, carbocyanine-type fluorophores, dipyrromethene boron-type fluorophores, coumarin-type fluorophores, acridine-type fluorophores, pyrene-type fluorophores, DANSYL-type fluorophores, and lanthanide chelate-type fluorophores. The second precursor may include an acceptor fluorophore selected from the group consisting of fluorescein-type fluorophores, rhodamine-type fluorophores, naphthalene-type fluorophores, coumarin-type fluorophores, and DANSYL-type fluorophores.

In some embodiments, the fluorophore may be derivatized to make its fluorescence spectrum pH independent between pH 6 and pH 8. For example, the fluorophore may be halogenated and suitable fluorophores may include a halogenated fluorescein-type fluorophore and a halogenated rhodamine-type fluorophore. In other embodiments, the fluorescein-type fluorophore is a derivative of fluorescein in which the carboxyl group is replaced with any group that cannot cyclize (e.g., an alkyl, haloalkyl, or halo group). In other embodiments, the fluorescein-type fluorophore is a derivative of fluorescein or an analog of fluorescein in which the carboxyl group is linked to the cyclic nitrogen atom of piperazine. In further embodiments, the fluorescein-type fluorophore is a derivative of fluorescein or an analog of fluorescein in which the hydroxyl groups are oxidized to ketones or replaced with alkoxy groups (e.g., methoxy or ethoxy).

In some embodiments of the methods for preparing dithio compounds, the dithio reagent may include reactive groups, (e.g., $X^1$ and $X^2$ each may include at least one amino group) and the first precursor and the second precursor each may include reactive groups (e.g., at least one amine-reactive group). Suitable reactive groups may include amine-reactive groups and carbonyl-reactive groups. Amine-reactive groups may include isothiocyanate groups, carboxyl groups, succinimidyl ester groups, and sulfonyl groups. Carbonyl-reactive groups may include amino groups and hydrazide. Suitable dithio reagents for preparing the dithio compounds may include cystamine and diaminophenyl disulfide. Suitable precursors include isothiocyanate-containing fluorophores, sulfonyl-containing fluorophores, carboxyl-containing fluorophores, and the like.

In some embodiments of the method, the first precursor and the second precursor each may include at least one amine-reactive groups and the dithio reagent has a formula $X^1$—S—S—$X^2$, where $X^1$ has the formula —$X^3$—$NH_2$; $X^2$ has the formula —$X^4$—$NH_2$; $X^3$ and $X^4$ may be the same or different and include groups independently selected from the groups consisting of $C_{1-18}$ alkyl groups, alkenyl groups, alkynyl groups, aryl groups and combinations thereof. In some embodiments $X^3$ and $X^4$ may be the same or different and include aryl groups. The dithio compounds described herein (and which may be prepared by the method) may have a formula D-$X^3$—S—S—$X^4$-A, where "D" includes a donor fluorophore and "A" include an acceptor fluorophore. $X^3$ and $X^4$ may be the same or different and may include aryl groups.

Also disclosed herein are dithio compounds having a formula D-S—S-A, in which "D" includes a donor fluorophore and "A" includes an acceptor non-fluorophore. In some suitable embodiments, the acceptor non-fluorophore is capable of quenching the donor fluorophore. The acceptor non-fluorophore may include a chromophore. The donor fluorophore may have an emission spectrum and the acceptor non-fluorophore may have an absorption spectrum, such that the emission spectrum and the absorption spectrum overlap. In some suitable embodiments, the emission spectrum and the absorption spectrum may overlap by about 20-100%, preferably by about 40-100%, more preferably by about 60-100%, and even more preferably by about 70-100%.

The dithio compounds may include a donor fluorophore and an acceptor non-fluorophore, such that the acceptor non-fluorophore is capable of quenching the donor fluorophore by dynamic quenching. The acceptor non-fluorophore may be capable of quenching the donor fluorophore by dynamic quenching that occurs by FRET. The acceptor non-fluorophore may be capable of quenching the donor fluorophore by static quenching.

The dithio compounds may include a donor fluorophore and an acceptor non-fluorophore that are present at a selected distance within the compounds. For example, the donor fluorophore and the acceptor non-fluorophore may be present in the dithio compounds at a distance of about 10-100 angstroms, preferably 25-75 angstroms, more preferably about 30-70 angstroms. In other embodiments, the donor fluorophore and the acceptor non-fluorophore may be present in the dithio compounds at a distance of about 3-100 angstroms, preferably 3-75 angstroms, more preferably about 3-50 angstroms. The donor fluorophore and the acceptor non-fluorophore may be present in the dithio compounds at a distance that is suitable to permit FRET. In some embodiments, the donor fluorophore and the acceptor non-fluorophore are present in the compound at a distance of no more than about 20 angstroms.

Also disclosed herein are dithio compounds having a formula D-S—S-A, in which "D" includes a donor fluorophore and "A" includes an acceptor fluorophore or non-fluorophore. In some embodiments, the acceptor fluorophore is capable of increasing or decreasing the absorption (extinction coefficient) for the donor fluorophore.

The dithio compounds may include any suitable donor fluorophore and acceptor non-fluorophore. In some embodiments, the donor fluorophore is selected from the group consisting of fluorescein-type fluorophores, rhodamine-type fluorophores, xanthene-type fluorophores, naphthalene-type fluorophores, carbocyanine-type fluorophores, and coumarin-type fluorophores. The acceptor non-fluorophore may be selected from the group consisting of dinitrophenol-type non-fluorophores, polyaromatic azo-type non-fluorophores, and rhodamine-type non-fluorophores.

Dithio compounds that include a donor fluorophore and an acceptor non-fluorophore may be prepared by any suitable method. For example, the dithio compounds may be prepared by reacting precursors that include: (A) a first precursor that includes a donor fluorophore; (B) a second precursor that includes an acceptor non-fluorophore; and (C) a dithio reagent having the formula $X^1$—S—S—$X^2$, where $X^1$ and $X^2$ may be the same or different and each includes at least one reactive group capable of reacting with the first precursor and the second precursor. The dithio reagent may comprise diamino phenyl disulfide and cystamine.

The dithio compounds described herein may have a formula D-$X^3$—S—S—$X^4$-A where "D" includes a donor fluorophore and "A" includes an acceptor non-fluorophore. $X^3$ and $X^4$ may be the same or different and may include $C_{1-18}$ alkyl groups, alkenyl groups, alkynyl groups, aryl groups and combinations thereof.

Also disclosed herein are dithio compounds having a formula D-S—S-A, in which "D" includes a radioisotope and "A" includes a scintillant. Suitable radioisotopes may include $^3H$, $^{14}C$, $^{35}S$, $^{32}P$, $^{33}P$, $^{125}I$, and $^{131}I$. The radioisotope may be covalently attached to the dithio compound or non-covalently associated with the dithio compound. Scintillants may include solid scintillants that are suitable for performing scintillation proximity assays.

Also disclosed herein are methods for detecting thiol-containing compounds. In some embodiments the methods include (A) reacting a reaction mixture to form at least one reaction product; and (B) detecting the at least one reaction product. Typically, the reaction mixture will include (i) the thiol-containing compound; and (ii) a dithio compound as described herein. For example, suitable dithio compounds for the methods for detecting thiol-containing compounds include dithio compounds having a formula D-S—S-A, in which "D" includes a donor fluorophore and "A" includes an acceptor fluorophore or an acceptor non-fluorophore. In the methods for detecting thiol-containing compounds as described herein, detecting the at least one reaction product may include observing dequenching of the donor fluorophore. Detecting the at least one reaction product may include observing a decrease in fluorescence polarization in the dithio compound. Detecting the at least one reaction product may also include measuring an increase or decrease in the absorbance spectrum for the donor fluorophore.

In some embodiments, the dithio compound includes an acceptor fluorophore. Detecting the at least one reaction product may include observing a decrease in sensitized fluorescence of the acceptor fluorophore.

The methods may be used to detect any suitable thiol-containing compound. For example, the methods may be used to detect thiol-containing compounds such glutathione, homocysteine, cysteine-containing peptides or proteins, ADPβS, GDPβS, and combinations thereof. The methods may be used to detect altered levels of thiols in cell walls or membranes, such as in bacterial cell walls or in the chorion of embryos. The methods may be used to detect thiols quantitatively, as in clinical or biochemical assays, or qualitatively, as in a histological stain for tissue samples.

The method may be used to detect thiol-containing compounds having a formula X—S—H, where the at least one reaction product has a formula selected from D-S—S—X, A-S—S—X, D-S—H, A-S—H, and salts thereof. Detecting the at least one reaction product may include detecting dequenched fluorescence or altered absorbance of the donor fluorophore in a reaction product having a formula selected from D-S—S—X, D-S—H, and salts thereof. In some embodiments, detecting the at least one reaction product may include detecting a decrease in sensitized fluorescence of the acceptor fluorophore in a reaction product having a formula selected from A-S—S—X, A-S—H, and salts thereof.

The methods for detecting thiol-containing compounds as described herein may be performed continuously or in real-time. The methods for detecting thiol-containing compounds may be performed in vitro, in vivo, and/or in situ.

Related dithio compounds and methods for using dithio compound are described in U.S. provisional application No. 60/715,090, filed on Sep. 8, 2005; Pullela et al., "Fluorescence-based detection of thiols in vitro and in vivo using dithiol probes," ANAL. BIOCHEM. (2006) 352(2):265-73; and in Chiku et al., "A Dithio Coupled Assay and ATPase assay," JOURNAL OF BIOMOLECULAR S$_{CREENING}$ 11(X); (2006) (accepted for publication Jun. 21, 2006); which are incorporated by reference herein in their entireties.

BRIEF DESCRIPTION OF THE DRAWINGS

FIG. 12. Selective detection of ADPβS versus ATPβS using F-DAPS-R: (a) reaction of 1 μM F-DAPS-R with 500 mM ADPβS or ATPβS; (b) schematic representation of the reaction of F-DAPS-R with ADTβS or ATPβS; (c) kinetic analysis of the reaction of 5 μM F-DAPS-R and 2.5 mM ADPβS.

FIG. 13. Comparison of common coupled kinase assay versus thiol-based F-DAPS-R coupled assay: (a) schematic representation of common coupled kinase assay, (i.e., pyruvate kinase/lactate dehydrogenase assay (PK/LDH assay)); (b) absorbance of $NAD^+$ versus NADH; (c) schematic representation of thiol-based F-DAPS-R coupled assay; (d) absorbance of F-DAPS-R versus F—S$^-$.

FIG. 14. Schematic representation of the reaction of DTT with fluorescein/rhodamine disulfide compound (represented as "F—S—S—R").

FIG. 15. Reaction of 5 μM fluorescein/rhodamine diamino phenyl disulfide compound (represented as "F—S—S—R") with selected thiols (2.5 mM) in 0.1 M Tris Buffer, pH 8.15, at 25° C.: (a) DTT; (b) ADPβS; (c) reduced glutathione (GS$^-$).

FIG. 16. Uptake of fluorescein/rhodamine diamino phenyl disulfide reagent (represented as "FITC-DAPS-Rh") and fluorescein/rhodamine cystamine reagent (represented as "FITC-CYST-Rh") into *E. coli* cells.

FIG. 17. Uptake of fluorescein/rhodamine diamino phenyl disulfide reagent "F-DAPS-R" into zebrafish embryo at 1 dpf (day post fertilization), localized in the chorion that surrounds the embryo.

FIG. 18. FRET-based detection of thiols: (a) $R^1$—S—S—$R^2$ probe with FRET capability (coumarin-DAP-FITC); (b) Fluorescence emission of coumarin-DAP-FITC at different excitation wavelengths; (c) Fluorescence emission of coumarin DAP-FITC after treatment with 1 mM DTT reductant (5 min) at different excitation wavelengths.

DETAILED DESCRIPTION

Figure 1:
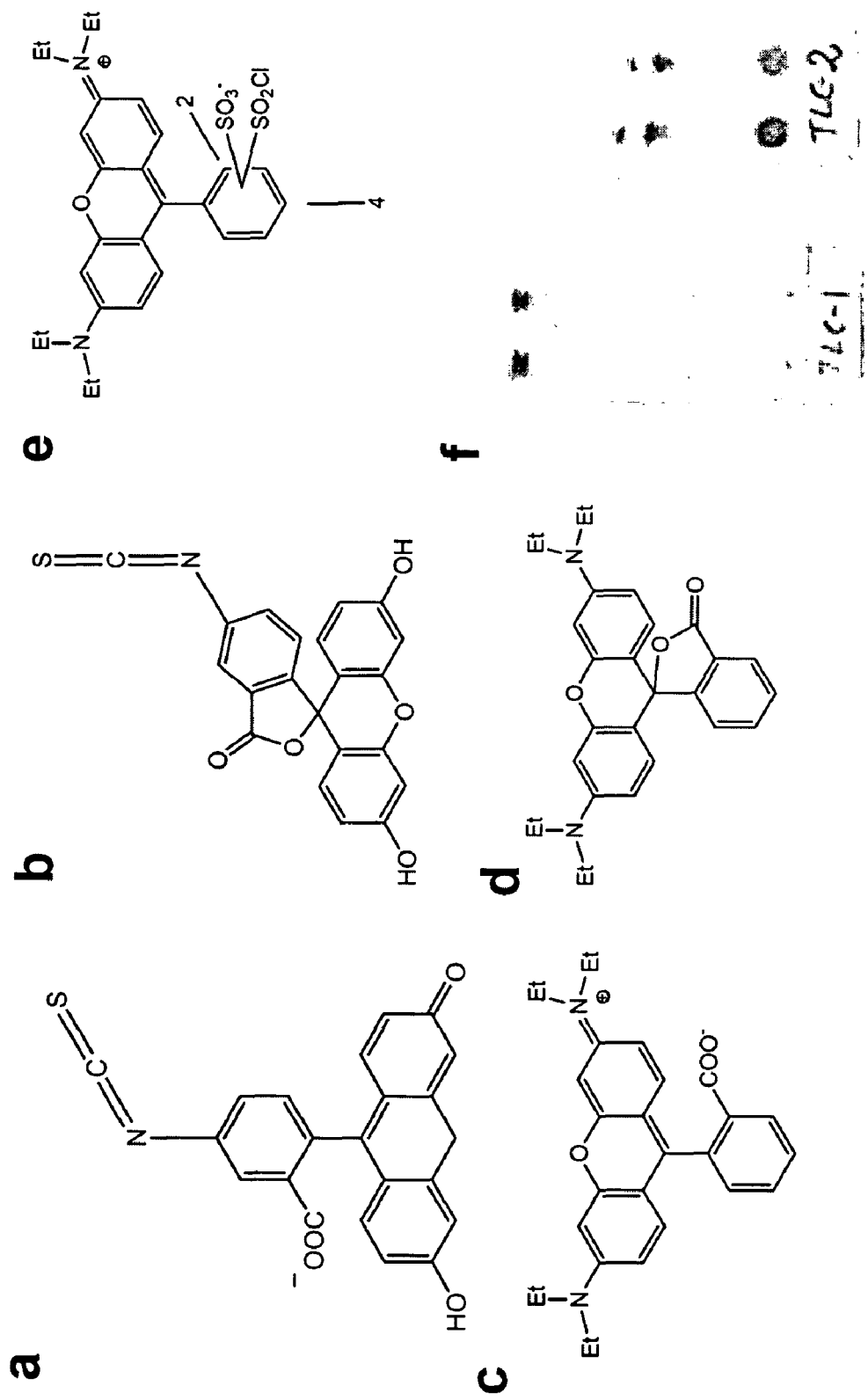
FIG. 1. Representation of fluorescein isothiocyanate (FITC): (a) at basic pH, and (b) acidic pH; representation of rhodamine-B: (c) at basic pH and (d) acidic pH; (e) Representation of RhSO$_2$Cl (rhodamine sulfonyl chloride); (f) Thin-layer chromatograph of sample of RhSO$_2$Cl obtained from two different commercial sources (left and right lanes of TLC-1 and TLC-2): TLC-1, MeOH:CHCl$_3$ (3:7); TLC-2, MeOH:CHCl$_3$ (1:9).
Figure 2:
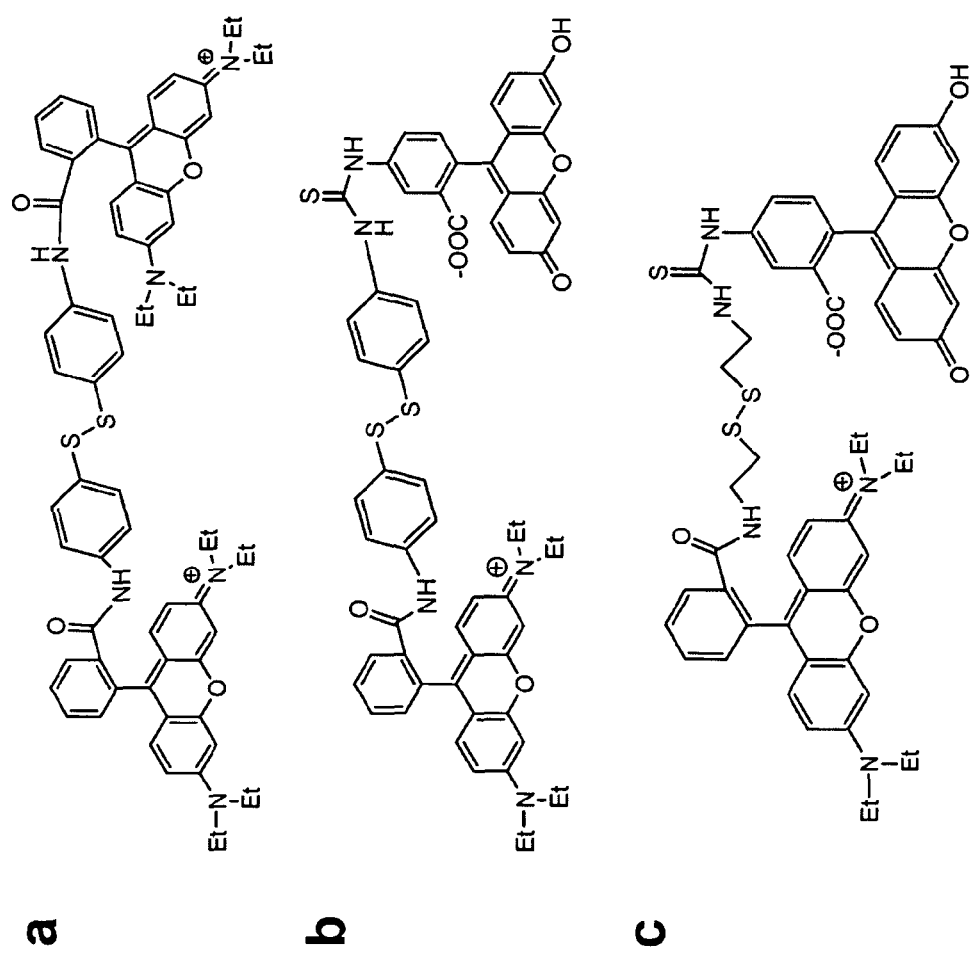
FIG. 2. Representation of dithio compounds obtained by (a) reaction of diamino phenyl disulfide and rhodamine B; (b) reaction of diamino phenyl disulfide, rhodamine B, and FITC; and (c) reaction of cystamine, rhodamine B, and FITC.

Disclosed herein are dithio compounds. The dithio compounds described herein may be used in methods for detecting thiol-containing compounds. For example, the dithio compounds may be reacted with thiol-containing compounds to detect the thiol-containing compounds.

As used herein, "dithio" means the chemical group —S—S—. A "dithio compound" is a compound that includes at least one chemical group —S—S—. As used herein, "dithio" is interchangeable with "disulfide."

As used herein, "thiol" means the chemical group —S—H or the ionized form of —S—H, i.e., —S—. A "thiol-containing compound" is a compound that includes at least one chemical group —S—H and/or —S—.

The dithio compounds described herein may have a formula D-S—S-A, where "D" includes a donor fluorophore and "A" includes an acceptor fluorophore. As used herein, a "fluorophore" is a chemical group that can be excited by light to emit fluorescence. Some suitable fluorophores may be excited by light to emit phosphorescence. As used herein, a "dye" may include a fluorophore. The dithio compounds described herein may include fluorophore selected from but not limited to: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy F1-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; Euko-Light; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, WV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3. As used herein, a "fluorophore" may include a salt of the fluorophore.

Fluorophores may include derivatives that have been modified to facilitate conjugation to another reactive molecule. As such, fluorophores may include amine-reactive derivatives such as isothiocyanate derivatives and/or succinimidyl ester derivatives of the fluorophore.

The dithio compounds may include a fluorophore selected from the group of xanthene-type fluorophores. The group of xanthene-type fluorophores typically includes any fluorophore that includes a xanthene group having the formula:

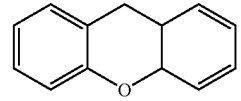

Xanthene-type fluorophores include fluorescein-type fluorophores (e.g., fluoroscein and fluorescein isothiocyanate, and the like) and rhodamine-type fluorophores (e.g., rhodamine, rhodamine-B, and the like).

The dithio compounds may include a fluorophore selected from the group of fluorescein-type fluorophores. The group of fluorescein-type fluorophores typically includes any fluorophore that includes a fluorescein group having the formula:

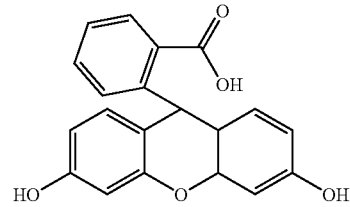

and derivatives and isomers thereof. Particularly useful derivatives include those with the carboxyl group replaced with any group that cannot cyclize (e.g., alkyl, haloalkyl, and halo groups). Other derivatives include those in which the carboxyl group is reacted with separate molecule (e.g., a nitrogen atom present in a separate molecule). For example, a derivative may be prepared by reacting fluorescein and piperazine where the carboxyl group of fluorescein reacts with the cyclic nitrogen atom of piperazine to form an amide linkage. The hydroxyl groups of the fluorescein molecule may be oxidized to ketones to form derivatives. The hydroxyl groups may be replaced with alkoxy groups to form derivatives (e.g., derivatives having methoxy or ethoxy groups in place of the hydroxyl groups).

Fluorescein-type fluorophores include fluorescein, fluorescein derivatives that include a fluorescein group, and salts thereof (e.g., 5-carboxy-2,7-dichlorofluorescein; 5-Carboxyfluorescein (5-FAM); DCFH (Dichlorodihydrofluorescein Diacetate); Fluorescein isothiocyanate (FITC); Fluorescein Diacetate, and the like).

The dithio compounds may include a fluorophore selected from the group of rhodamine-type fluorophores. The group of rhodamine-type fluorophores typically includes any fluorophore that includes a rhodamine group having the formula:

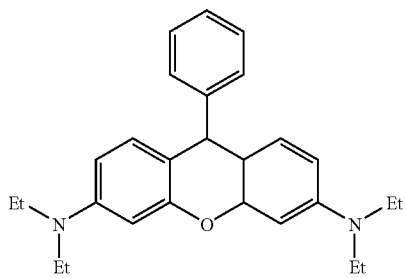

and isomers thereof.

Rhodamine-type fluorophores include rhodamine, rhodamine derivatives that include a rhodamine group, and salts thereof (e.g., 5-Carboxytetramethylrhodamine (5-TAMRA); 5-ROX (carboxy-X-rhodamine); 6-Carboxyrhodamine 6G; DHR (Dihydorhodamine 123); Lissamine Rhodamine; Lissamine Rhodamine B; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Sulphorhodamine B can C; Sulphorhodamine G Extra; Tetramethylrhodamine (TRITC); X-Rhodamine; XRITC, and the like).

The dithio compounds may include a fluorophore selected from the group of the naphthalene-type fluorophores. The naphthalene-type fluorophores typically include any fluorophore that includes a naphthalene group having the formula:

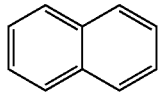

Naphthalene-type fluorophores include naphthalene, IAEDANS, EDANS, and the like. Naphthalene-type fluorophores may include pyrene.

In some embodiments, the acceptor fluorophore is different from the donor fluorophore and is capable of at least one of: (a) quenching the donor fluorophore; (b) increasing or decreasing the absorption spectrum for the donor fluorophore, and (c) sensitized emission when excited by the donor fluorophore. The donor fluorophore may have a maximum absorbance ($Abs_{max}$) for light of a particular wavelength ($\lambda$) that differs from the $Abs_{max}$ of the acceptor fluorophore. For example, the acceptor fluorophore and the donor fluorophore may have maximum absorbances for light having wavelengths that differ by at least about 10 nm, preferably 15 nm, more preferably 20 nm, and even more preferably 25 nm. The donor fluorophore may have a maximum emission ($Em_{max}$) for light of a particular wavelength that differs from the $Em_{max}$ of the acceptor fluorophore. For example, the acceptor fluorophore and the donor fluorophore may have maximum emissions for light having wavelengths that differ by at least about 10 nm, preferably 15 nm, more preferably 20 nm, and even more preferably 25 nm.

In some embodiments, the donor fluorophore has an emission spectrum and the acceptor fluorophore has an absorption spectrum, such that the emission spectrum and absorption spectrum overlap. In particular, the emission spectrum and the absorption spectrum may overlap by about 20-100%, preferably about 40-100%, more preferably about 60-100%, and even more preferably about 70-100%. Overlap may be determined by determining the integral (i.e., area under the curve) for the absorbance versus wavelength for a given range of wavelengths (e.g., $\lambda$=450-750 nm) for any selected donor fluorophore and any selected acceptor fluorophore.

The dithio compounds may include a donor fluorophore and an acceptor fluorophore such that the acceptor fluorophore is capable of quenching the donor fluorophore. Quenching may include dynamic quenching, static quenching, or both. Dynamic quenching may occur by FRET. Quenching may be relieved when the dithio group of the dithio compound is reduced, e.g., by reacting the dithio compound with a thiol-group that reduces the dithio compound.

The dithio compounds may include a donor fluorophore and an acceptor fluorophore such that the acceptor fluorophore is capable of altering the absorbance spectrum of the donor fluorophore. This alteration in absorbance may be relieved when the dithio group of the dithio compound is reduced, e.g., by reacting the dithio compound with a thiol-group that reduces the dithio compound.

The dithio compounds may include a donor fluorophore and an acceptor fluorophore such that the donor fluorophore is capable of inducing sensitized emission in the acceptor fluorophore, e.g., inducing sensitized emission by FRET. Sensitized emission may be reduced when the dithio bond of the dithio compound is cleaved, e.g., by reacting the dithio compound with a thiol-group that reduces the dithio compound.

The dithio compounds may include a donor fluorophore and an acceptor fluorophore that are present at a selected distance within the compounds, e.g., at a distance of about 6-100 angstroms, preferably 15-75 angstroms, more preferably about 30-70 angstroms. In some embodiments, the donor fluorophore and the acceptor fluorophore are present at a distance of about 3-100 angstroms, preferably 3-75 angstroms, more preferably about 3-50 angstroms. The donor fluorophore and the acceptor fluorophore may be present in the dithio compounds at a distance that is suitable to permit FRET. In some embodiments, the donor fluorophore and the acceptor fluorophore are present in the compound at a distance of no more than about 20 angstroms. The donor fluorophore and the acceptor fluorophore may be present in the dithio compounds at a distance that is suitable for static quenching.

Typically, in a dithio compound capable of exhibiting FRET, the donor fluorophore and acceptor fluorophore will be within 10-100 Å (e.g., 6-100 Å) in the intact FRET dithio compound; the absorption spectrum of the acceptor fluorophore and emission spectrum of the donor fluorophore will overlap; and the donor-acceptor transition dipole orientations will be parallel for a significant fraction of time during the assay. One parameter in a FRET reagent is the Forster radius, which may be defined as the distance at which energy transfer is 50% efficient, and is given by the equation:

$$R_o = [8.8 \times 10^{23} * \lambda^2 * n^4 QY_D * J(\lambda)]^{1/6} \text{Å}$$

where n is the refractive index, $J(\lambda)$ is the spectral overlap integral, $\lambda^2$ is the dipole orientation factor (⅔ if randomly oriented), and $QY_D$ is the quantum yield for the donor in the absence of the acceptor. Efficiency of energy transfer increases to about 50% at distances less than $R_o$.

The distance between the donor fluorophore and the acceptor fluorophore may be designed by selecting a dithio linker that has a selected length. As used herein, a dithio linker may have a formula —$X^1$—S—S—$X^2$—, the $X^1$ group and the $X^2$ group may be the same or different and selected from $C_{1-18}$ alkyl groups, alkenyl groups, alkynyl groups, aryl groups and combinations thereof, optionally substituted with at least one reactive group (e.g., —$NH_2$). The length of the dithio linker may be designed by selecting a suitable $X^1$ group and a suitable $X^2$ group, e.g., an $X^1$ group and an $X^2$ group that have a suitable number of carbon atoms to provide a selected length for the dithio linker.

The dithio compound may have a formula D-$X^1$—S—S—$X^2$-A, in which "D" includes a donor fluorophore and "A" includes an acceptor fluorophore, and at least one of the $X^1$ group and the $X^2$ group include a chemical group that is capable of influencing at least one of the emission spectrum and absorbance spectrum of the donor fluorophore. At least one of the $X^1$ group and the $X^2$ group may include a chemical group that is capable of influencing at least one of the emission spectrum and absorbance spectrum of the acceptor fluorophore. At least one of the $X^1$ group and the $X^2$ group may include an aryl group. In some embodiments, the aryl group may be selected from a phenyl group and a pyridinyl group, which may be optionally substituted with at least one of alkyl groups, haloalkyl groups, halogen groups, alkyl ester groups, ether groups, carboxyl groups, amide groups, and nitro groups.

For example, at least one of $X^1$ and $X^2$ may include an aryl group. The aryl group may be substituted with an amide group. In some embodiments at least one of $X^1$ and $X^2$ includes a group having a formula selected from:

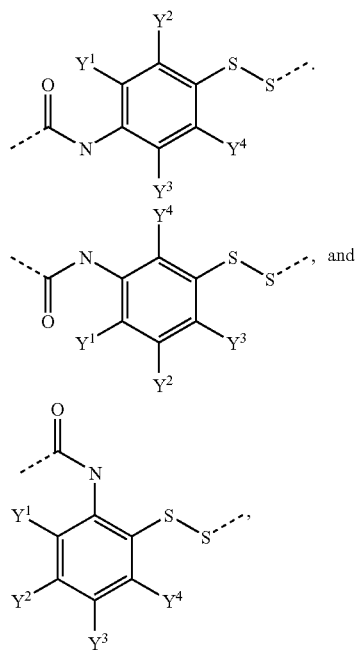

wherein $Y^1$, $Y^2$, $Y^3$, and $Y^4$ may be the same or different and are hydrogen or halide (i.e., H, F, Cl, Br, or I).

In one suitable embodiment, at least one of $X^1$ and $X^2$ includes a group having a formula:

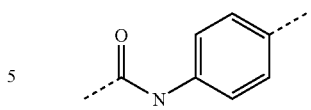

The dithio compound may include derivatives of cystamine or diaminodiphenyldisulfide (herein referred to as "DAPS"). In some embodiments, the dithio compound may include derivatives of p,p'-diaminodiphenyldisulfide, m,m'-diaminodiphenyldisulfide, and o,o'-diaminodiphenyldisulfide.

In one suitable embodiment, the dithio compound has the formula:

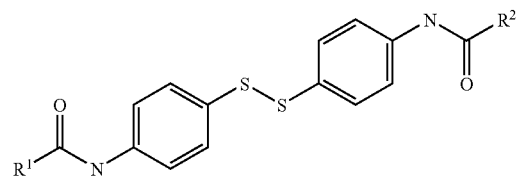

in which $R^1$ includes a fluorophore group and $R^2$ includes a fluorophore group or a non-fluorophore group.

The dithio compounds may include a donor fluorophore and an acceptor fluorophore that are known in the art to undergo FRET. For example, a suitable donor fluorophore may include a fluorescein-type fluorophore (e.g., FITC) and a suitable acceptor fluorophore may include a rhodamine-type fluorophore (e.g., rhodamine B).

The dithio compound may have a formula:

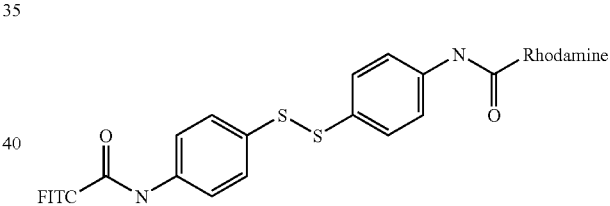

(referred to herein interchangeably as "FITC-DAPS-R" or "Rh-DAPS-FITC").

"F—S—S—R" and "R—S—S—F" are used interchangeably herein to refer to a dithio compound that includes a fluorescein-type fluorophore and a rhodamine-type fluorophore linked by a dithio linker. "F-DAPS-R" and "R-DAPS-S" are used interchangeably herein to refer to a dithio compound that includes a fluorescein-type fluorophore and a rhodamine-type fluorophore linked by a diaminodiphenyldisulfide linker, (which may include p,p'-diaminodiphenyldisulfide linkers, m,m'-diaminodiphenyldisulfide linkers, and o,o'-diaminodiphenyldisulfide linkers). "F-CYST-R" and "R-CYST-F" are used interchangeably herein to refer to a dithio compound that includes a fluorescein-type fluorophore and a rhodamine-type fluorophore linked by a cystamine linker.

The dithio compounds may include a FRET pair as follows: a donor fluorophore selected selected from a group consisting of fluorescein-type fluorophores, rhodamine-type fluorophores, xanthine-type fluorophores, naphthalene-type fluorophores, carbocyanine-type fluorophores, dipyrromethene boron-type fluorophores, coumarin-type fluorophores, acridine-type fluorophores, pyrene-type fluorophores, DANSYL-type fluorophores, and lanthanide chelate-type fluorophores; and an acceptor fluorophore selected from a group consisting of fluorescein-type fluorophores, rhodamine-type fluorophores, naphthalene-type fluorophores, coumarin-type fluorophores, and DANSYL-type fluorophores.

The dithio compounds may include a fluorescein-type fluorophore as a donor fluorophore and a rhodamine-type fluorophore as an acceptor fluorophore, which are present in the dithio compounds at a distance of about 10-60 angstroms (e.g., 40-60 angstroms). The dithio compounds may include a naphthalene-type fluorophore as a donor fluorophore and a fluorescein-type fluorophore as an acceptor fluorophore, which are present in the dithio compounds at a distance of about 10-60 angstroms (e.g., 40-60 angstroms). The dithio compounds may include a DANSYL-type fluorophore as a donor fluorophore and a fluorescein-type fluorophore as an acceptor fluorophore, which are present in the dithio compounds at a distance of about 10-50 angstroms (e.g., 25-45 angstroms).

The dithio compounds may be prepared by any suitable method. For example, the dithio compounds may be prepared by reacting a reaction mixture that includes: (a) a dithio linking agent with two or more first reactive groups; (b) a donor fluorophore having at least one second reactive group; and (c) an acceptor fluorophore having a third reactive group. The second and third reactive groups may be the same or different. In some embodiments, the donor fluorophore (or acceptor fluorophore) may be reacted with the dithio linker to form an intermediate reaction product that is at least partially purified and subsequently reacted with the acceptor fluorophore (or donor fluorophore, respectively). Suitable reactive groups may include nucleophilic groups and electrophilic groups, (e.g., nucleophilic groups and electrophilic groups capable of reacting with each other). Reactive groups may include amino groups and amine-reactive groups (e.g., isothiocyanate groups, succinimidyl ester groups, carboxyl groups, sulfonyl groups, and the like). Suitable dithio linking agents for preparing the dithio compounds may include cystamine and diaminophenyl disulfide.

Amine-reactive fluorophores may be derivatized by reacting with groups such as isothiocyanates (yielding thioureas) or succinimidyl esters (yielding carboxamides). Reactions then may be performed with dithio linking reagents that include a reactive amine (e.g., —NH$_2$) and a dithio group. For example, the dithio linking reagent may a formula NH$_2$—X$^1$—S—S—X$^2$—NH$_2$, in which X$^1$ and X$^2$ may be the same or different and may include C$_{1-18}$ (preferable C$_{1-18}$) alkyl, alkenyl, alkynyl, or aryl, which may be optionally substituted with at least one heteroatom selected from N, P, and O. To separate reaction products (e.g., D-S—S-D, D-S—S-A and A-S—S-A, where D=donor fluorophore and A=acceptor fluorophore) HPLC may be performed. Useful reagents for synthesizing FRET reagents may include cysteine, β-mercaptoethaneamine, cystamine, diamino phenyl disulfide, and mixtures thereof.

Also disclosed herein are dithio compounds having a formula D-S—S-A, in which "D" includes a donor fluorophore and "A" includes an acceptor non-fluorophore. In some suitable embodiments, the acceptor non-fluorophore is capable of quenching the donor fluorophore. The acceptor non-fluorophore may include a chromophore. Non-fluorophores may include dyes. Suitable non-fluorophores may include dark quenchers. For example, suitable non-fluorophore dark quenchers may include azobenzene dyes such as Dabcyl-type non-fluorophores, and Dabsyl-type non-fluorophores. The non-fluorophore dark quencher may include polyaromatic azo-type non-fluorophores which include polymers having a formula:

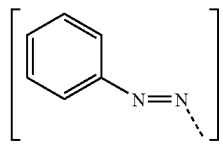

which may be optionally substituted with alkyl groups, alkyl ester groups, and/or nitro groups. Dark quenchers may include black hole quenchers sold under the tradename "BHQ" (e.g., BHQ-0, BHQ-1, BHQ-2, and BHQ-3, Biosearch Technologies, Novato, Calif.). Dark quenchers may include quenchers sold under the tradename "QXL™" (Anaspec, San Jose, Calif.). Dark quenchers may include DNP-type non-fluorophores that include a 2,4-dinitrophenyl group.

The dithio compounds may include a donor fluorophore and an acceptor non-fluorophore, such that the acceptor non-fluorophore is capable of quenching the donor fluorophore by dynamic quenching, static quenching, or both. The acceptor non-fluorophore may be capable of quenching the donor fluorophore by dynamic quenching that occurs by FRET.

The dithio compounds may include a donor fluorophore and an acceptor non-fluorophore that are present at a selected distance within the compounds. For example, the donor fluorophore and the acceptor non-fluorophore may be present in the dithio compounds at a distance suitable for FRET (e.g., about 10-100 angstroms, preferably 25-75 angstroms, more preferably about 30-70 angstroms). In some embodiments, the donor fluorophore and the acceptor non-fluorophore are present at a distance suitable for FRET such as about 3-100 angstroms, preferably 3-75 angstroms, more preferably about 3-50 angstroms. The donor fluorophore and the acceptor non-fluorophore may be present in the dithio compounds at a distance that is suitable to permit static quenching (e.g., at a distance of no more than about 20 angstroms).

The dithio compounds may include any suitable donor fluorophore and acceptor fluorophore pair including: a fluorophore selected from the group consisting of fluorescein-type fluorophores, rhodamine-type fluorophores, naphthalene-type fluorophores, carbocyanine-type fluorophores, and coumarin-type fluorophores; and an acceptor non-fluorophore selected from the group consisting of dinitrophenol-type non-fluorophores, polyaromatic azo-type non-fluorophores, and rhodamine-type non-fluorophores.

Dithio compounds that include a donor fluorophore and an acceptor non-fluorophore may be prepared by any suitable method including methods suitable for preparing dithio compounds that include a donor fluorophore and an acceptor fluorophore as described herein. For example, the dithio compounds may be prepared by reacting precursors that include: (A) a first precursor that includes a donor fluorophore; (B) a second precursor that includes an acceptor non-fluorophore; and (C) a dithio reagent (i.e., a dithio linking reagent) having the formula X$^1$—S—S—X$^2$, where X$^1$ and X$^2$ may be the same or different and each includes at least one reactive group capable of reacting with the first precursor and the second precursor. The donor fluorophore and the acceptor fluorophore may include reactive groups as described herein. The dithio compounds that include a donor fluorophore and an acceptor non-fluorophore (and which may be prepared by the methods described herein) may have a formula D-$X^3$—S—S—$X^4$-A where "D" includes a donor fluorophore and "A" includes an acceptor non-fluorophore. $X^3$ and $X^4$ may be the same or different and may include aryl groups.

Also disclosed herein are dithio compounds having a formula D-S—S-A, in which "D" includes a radioisotope and "A" includes a scintillant. Suitable radioisotopes may include $^3$H, $^{14}$C, $^{35}$S, $^{32}$P, $^{33}$P, $^{125}$I, and $^{131}$I. The radioisotope may be covalently attached to the dithio compound. In some embodiments the radioisotope may be non-covalently associated with the dithio compound. For example, "D" may include a chelating agent that chelates the selected radioisotope. Suitable chelating agents may include ethylene diamine tetracetic acid (EDTA) and nitrilo triacetate (NTA). Scintillants include solid scintillants that are suitable for performing scintillation proximity assays. The scintillant may be covalently attached to the dithio compound or non-covalently associated with the dithio compound.

Also disclosed herein are dithio compounds having a formula D-S—S-A, in which "D" includes a fluorophore and "A" includes any molecule with a molecular weight about 2× larger than D, (or preferably about 4× larger than D, or more preferably about 10× larger than D). In some embodiments, reduction of the disulfide bond leads to a 20% decrease (or preferably a 40% decrease, or more preferably a 60% decrease) in a fluorescence polarization signal detectable from "D".

Also disclosed herein are methods for detecting thiol-containing compounds. In some embodiments the methods include (A) reacting a reaction mixture to form at least one reaction product; and (B) detecting the at least one reaction product. Typically, the reaction mixture will include (i) the thiol-containing compound; and (ii) a dithio compound as described herein. The reaction mixture may be formed in vitro, in vivo, or in situ. The reaction mixture may be present in a cell. The dithio compounds may be used to detect thiol-containing compounds in biopsy methods. The dithio compounds may be used to detect thiol-containing compounds by monitoring tissue sample fluorescence levels quantitatively in a fluorimeter or with a fluorescence microscope, or qualitatively by using the disclosed dithio compounds as a component of a histological stain. Methods for using the dithio compounds disclosed herein for detecting thiol-containing compounds are described in U.S. provisional application No. 60/715,090, which is incorporated herein by reference.

Suitable dithio compounds for the methods for detecting thiol-containing compounds include dithio compounds having a formula D-S—S-A, in which "D" includes a donor fluorophore and "A" includes an acceptor fluorophore or an acceptor non-fluorophore. In the methods for detecting thiol-containing compounds as described herein, detecting the at least one reaction product may include observing dequenching of the donor fluorophore or altered absorbance of the donor. In the method, detecting the at least one reaction product may include observing a decrease in sensitized emission of an acceptor fluorophore. Detecting the at least one reaction product may include observing a decrease in fluorescence polarization in the dithio compound.

The methods may be used to detect any suitable thiol-containing compound. Suitable thiol-containing compounds include any thiol-containing compound that is capable of reducing the dithio compound. For example, the methods may be used to detect thiol-containing compounds such as glutathione, homocysteine, cysteine-containing peptides or proteins, ADPβS, GDPβS, and combinations thereof. The methods for detecting thiol-containing compounds may be performed in vitro, in vivo, and/or in situ. The methods may be performed in cells. For example, the methods may be performed by administering the dithio compounds to tissue or cells in which the compounds react with at least one thiol-containing compound to form at least one reaction product.

The methods may include detecting the at least one reaction product, e.g., by fluoroscopic methods known in the art. Detecting the at least one reaction product may include detecting dequenched fluorescence of the donor fluorophore in a reaction product using fluoroscopic methods known in the art. Detecting the at least one reaction product may include detecting an increase or decrease in absorbance by the donor fluorophore using fluoroscopic methods known in the art. Detecting the at least one reaction product may include detecting a decrease in sensitized fluorescence of the acceptor fluorophore in a reaction product using fluoroscopic methods known in the art.

The methods for detecting thiol-containing compounds as described herein may be performed continuously or in real-time. As used herein, "real-time" methods are methods in which the thiol-containing compound is detected contemporaneously as it is formed in a reaction mixture (e.g., as it is formed in vitro or in cells).

Illustrative Embodiments

The following embodiments are illustrative and not intended to limit the claimed subject matter.

Embodiment 1. A dithio compound having a formula D-S—S-A, wherein D comprises a donor fluorophore; and A comprises an acceptor fluorophore that is different from the donor fluorophore and that is capable of at least one of: (a) quenching the donor fluorophore; (b) increasing or decreasing an extinction coefficient of the donor fluorophore; and (b) sensitized emission when excited by the donor fluorophore.

Embodiment 2. The compound of embodiment 1, wherein the donor fluorophore has an absorbance maximum and the acceptor fluorophore has an absorbance maximum that differ by at least about 10 nm, preferably 15 nm, more preferably 20 nm, even more preferably 25 nm.

Embodiment 3. The compound of embodiment 1, wherein the donor fluorophore has an emission maximum and the acceptor fluorophore has an emission maximum that differ by at least about 10 nm, preferably 15 nm, more preferably 20 nm, even more preferably 25 nm.

Embodiment 4. The compound of embodiment 1, wherein the donor fluorophore has an emission spectrum and the acceptor fluorophore has an absorption spectrum, such that the emission spectrum and absorption spectrum overlap.

Embodiment 5. The compound of embodiment 4, wherein the emission spectrum and the absorption spectrum overlap by about 20-100%, preferably about 40-100%, more preferably about 60-100%, and even more preferably about 70-100%.

Embodiment 6. The compound of embodiment 1, wherein the acceptor fluorophore is capable of quenching the donor fluorophore by dynamic quenching.

Embodiment 7. The compound of embodiment 6, wherein the dynamic quenching occurs by fluorescence resonance energy transfer.

Embodiment 8. The compound of embodiment 1, wherein the acceptor fluorophore is capable of quenching the fluorophore by static quenching.

Embodiment 9. The compound of embodiment 1, wherein the sensitized emission includes fluorescence.

Embodiment 10. The compound of embodiment 1, wherein the sensitized emission occurs by fluorescence resonance energy transfer.

Embodiment 11. The compound of embodiment 1, wherein the donor fluorophore and the acceptor fluorophore are present in the compound at a distance of about 3-100 angstroms, preferably 3-75 angstroms, more preferably about 3-50 angstroms.

Embodiment 12. The compound of embodiment 1, wherein the donor fluorophore and the acceptor fluorophore are present in the compound at a distance of no more than about 20 angstroms.

Embodiment 13. The compound of embodiment 1, wherein the donor fluorophore comprises a xanthene-type fluorophore.

Embodiment 14. The compound of embodiment 13, wherein the xanthene-type fluorophore includes a fluorescein-type fluorophore.

Embodiment 15. The compound of embodiment 1, wherein the acceptor fluorophore comprises a xanthene-type fluorophore.

Embodiment 16. The compound of embodiment 15, wherein the xanthene-type fluorophore comprises a rhodamine-type fluorophore, which optionally is halogenated to make its fluorescence spectrum pH independent between pH 6 and 8.

Embodiment 17. The compound of embodiment 1, wherein the donor fluorophore is selected from the group consisting of fluorescein-type fluorophores, rhodamine-type fluorophores, naphthalene-type fluorophores, carbocyanine-type fluorophores, dipyrromethene boron-type fluorophores, coumarin-type fluorophores, acridine-type fluorophores, pyrene-type fluorophores, DANSYL-type fluorophores, and lanthanide chelate-type fluorophores.

Embodiment 18. The compound of embodiment 1, wherein the acceptor fluorophore is selected from the group consisting of fluorescein-type fluorophores, rhodamine-type fluorophores, naphthalene-type fluorophores, coumarin-type fluorophores, and DANSYL-type fluorophores.

Embodiment 19. The compound of embodiment 1, wherein the donor fluorophore comprises a fluorescein-type fluorophore and the acceptor fluorophore comprises a rhodamine-type fluorophore, which fluorophores optionally are halogenated to make their fluorescence spectrum pH independent between pH 6 and 8.

Embodiment 20. The compound of embodiment 19, wherein the fluorescein-type fluorophore and the rhodamine-type fluorophore are present in the compound at a distance of about 40-60 angstroms.

Embodiment 21. The compound of embodiment 1, wherein the donor fluorophore comprises a naphthalene-type fluorophore and the acceptor fluorophore comprises a fluorescein-type fluorophore.

Embodiment 22. The compound of embodiment 21, wherein the naphthalene-type fluorophore and the fluorescein-type fluorophore are present in the compound at a distance of about 40-60 angstroms.

Embodiment 23. The compound of embodiment 1, wherein the donor fluorophore comprises a DANSYL-type fluorophore and the acceptor fluorophore comprises a fluorescein-type fluorophore.

Embodiment 24. The compound of embodiment 23, wherein the DANSYL-type fluorophore and the fluorescein-type fluorophore are present in the compound at a distance of about 25-45 angstroms.

Embodiment 25. The compound of embodiment 1, wherein the compound is prepared from precursors comprising: (A) a first precursor comprising a fluorescein-type fluorophore; (B) a second precursor comprising a rhodamine-type fluorophore; (C) a dithio reagent having the formula $X^1$—S—S—$X^2$, wherein $X^1$ and $X^2$ may be the same or different and comprise reactive groups capable of reacting with the first precursor and the second precursor; wherein, optionally, the fluorescein-type fluorophore and rhodamine-type fluorophore are halogenated to make their fluorescence spectra pH independent between pH 6 and 8.

Embodiment 26. The compound of embodiment 1, wherein the compound is prepared from precursors comprising: (A) a first precursor comprising a naphthalene-type fluorophore; (B) a second precursor comprising a rhodamine-type fluorophore; (C) a dithio reagent having the formula $X^1$—S—S—$X^2$, wherein $X^1$ and $X^2$ may be the same or different and comprise reactive groups capable of reacting with the first precursor and the second precursor.

Embodiment 27. The compound of embodiment 1, wherein the compound is prepared from precursors comprising: (A) a first precursor comprising a DANSYL-type fluorophore; (B) a second precursor comprising a fluorescein-type fluorophore; (C) a dithio reagent having the formula $X^1$—S—S—$X^2$, wherein $X^1$ and $X^2$ may be the same or different and comprise reactive groups capable of reacting with the first precursor and the second precursor.

Embodiment 30. A method for preparing the compound of embodiment 1 comprising reacting precursors that include: (A) a first precursor that comprises a donor fluorophore; (B) a second precursor that comprises an acceptor fluorophore; and (C) a dithio reagent having the formula $X^1$—S—S—$X^2$, wherein $X^1$ and $X^2$ may be the same or different and each comprise reactive groups capable of reacting with the first precursor and the second precursor.

Embodiment 31. The method of embodiment 30, wherein the donor fluorophore is selected from the group consisting of fluorescein-type fluorophores, rhodamine-type fluorophores, naphthalene-type fluorophores, carbocyanine-type fluorophores, dipyrromethene boron-type fluorophores, coumarin-type fluorophores, acridine-type fluorophores, pyrene-type fluorophores, DANSYL-type fluorophores, and lanthanide chelate-type fluorophores.

Embodiment 32. The method of embodiment 30, wherein the acceptor fluorophore is selected from the group consisting of fluorescein-type fluorophores, rhodamine-type fluorophores, naphthalene-type fluorophores, coumarin-type fluorophores, and DANSYL-type fluorophores.

Embodiment 33. The method of embodiment 30, wherein the dithio reagent comprises amino groups and the first precursor and the second precursor each include amine-reactive groups.

Embodiment 34. The method of embodiment 33, wherein the amine-reactive groups are selected from groups consisting of isothiocyanate groups, carboxyl groups, and succinimidyl ester groups.

Embodiment 35. The method of embodiment 33, wherein the dithio reagent is selected from cystamine and diaminophenyl disulfide.

Embodiment 36. The method of embodiment 30, wherein $X^1$ has the formula $X^3$—$NH_2$; $X^2$ has the formula $X^4$—$NH_2$; $X^3$ and $X^4$ may be the same or different and include groups independently selected from the groups consisting of $C_{1-18}$ alkyl groups, alkenyl groups, alkynyl groups, aryl groups and combinations thereof.

Embodiment 37. The method of embodiment 30, wherein $X^1$ has the formula $X^3$—$NH_2$; $X^2$ has the formula $X^4$—$NH_2$; $X^3$ and $X^4$ may be the same or different and include aromatic groups.

Embodiment 38. A dithio compound having a formula D-S—S-A, wherein D comprises a donor fluorophore; and A comprises an acceptor non-fluorophore that is capable of quenching the donor fluorophore.

Embodiment 39. The compound of embodiment 38, wherein the non-fluorophore comprises a chromophore.

Embodiment 40. The compound of embodiment 39, wherein the donor fluorophore has an emission spectrum and the acceptor non-fluorophore has an absorption spectrum, such that the emission spectrum and absorption spectrum overlap.

Embodiment 41. The compound of embodiment 40, wherein the emission spectrum and the absorption spectrum overlap by about 20-100%, preferably about 40-100%, more preferably about 60-100%, and even more preferably about 70-100%.

Embodiment 42. The compound of embodiment 38, wherein the acceptor non-fluorophore is capable of quenching the donor fluorophore by dynamic quenching.

Embodiment 43. The compound of embodiment 42, wherein the dynamic quenching occurs by fluorescence resonance energy transfer.

Embodiment 44. The compound of embodiment 38, wherein the acceptor non-fluorophore is capable of quenching the fluorophore by static quenching.

Embodiment 45. The compound of embodiment 38, wherein the donor fluorophore and the acceptor non-fluorophore are present in the compound at a distance of about 6-100 angstroms, preferably 15-75 angstroms, more preferably about 30-70 angstroms.

Embodiment 46. The compound of embodiment 38, wherein the donor fluorophore and the acceptor non-fluorophore are present in the compound at a distance of no more than about 20 angstroms.

Embodiment 47. The compound of embodiment 38, wherein the donor fluorophore is selected from the group consisting of fluorescein-type fluorophores, rhodamine-type fluorophores, naphthalene-type fluorophores, carbocyanine-type fluorophores, and coumarin-type fluorophores, wherein, optionally, the donor fluorophore is halogenated to make the fluorescence spectra pH independent between pH 6 and pH 8.

Embodiment 48. The compound of embodiment 38, wherein the acceptor non-fluorophore is selected from the group consisting of a nitrophenol-type non-fluorophore, a dinitrophenol-type non-fluorophores, polyaromatic azo-type non-fluorophores, and rhodamine-type non-fluorophores.

Embodiment 49. A dithio compound having a formula D-S—S-A, wherein D comprises a fluorophore; and A comprises a non-fluorophore that is capable of altering an absorption spectrum of the fluorophore.

Embodiment 50. A dithio compound having a formula D-S—S-A, wherein D comprises a fluorophore; and A comprises a non-fluorophore with a molecular weight about 2× larger than D, (preferably 4× larger than D, or more preferably 10× larger than D), such that reduction of the compound results in an observed decrease in a fluorescence polarization signal of D.

Embodiment 51. A method for preparing the compound of any of embodiments 38, 49, or 50 comprising reacting precursors that include: (A) a first precursor that comprises a donor fluorophore; (B) a second precursor that comprises an acceptor non-fluorophore; and (C) a dithio reagent having the formula $X^1$—S—S—$X^2$, wherein $X^1$ and $X^2$ may be the same or different and each comprise reactive groups capable of reacting with the first precursor and the second precursor.

Embodiment 52. A method for detecting a thiol-containing compound, comprising: (A) reacting a reaction mixture to form at least one reaction product, the reaction mixture comprising: (i) the thiol-containing compound and (ii) a reagent comprising the compound of embodiment 1; and (B) detecting the at least one reaction product.

Embodiment 53. The method of embodiment 52, wherein detecting the at least one reaction product is performed in real-time.

Embodiment 54. The method of embodiment 52, wherein detecting the at least one reaction product comprises observing dequenching of the donor fluorophore.

Embodiment 55. The method of embodiment 52, wherein detecting the at least one reaction product comprises observing a change in the absorbance spectrum of the donor fluorophore.

Embodiment 56. The method of embodiment 52, wherein detecting the at least one reaction product comprises observing a decrease in the fluorescence polarization of the donor fluorophore.

Embodiment 57. The method of embodiment 52, wherein detecting the at least one reaction product comprises observing a decrease in sensitized fluorescence of the acceptor fluorophore.

Embodiment 58. The method of embodiment 52, wherein the thiol-containing compound includes glutathione.

Embodiment 59. The method of embodiment 52, wherein the thiol-containing compound includes homocysteine.

Embodiment 60. The method of embodiment 52, wherein the thiol-containing compound includes a cysteine-containing peptide.

Embodiment 61. The method of embodiment 52, wherein the thiol-containing compound includes ADPβS, GDPβS, or mixtures thereof.

Embodiment 62. The method of embodiment 52, wherein the thiol-containing compound has a formula X—S—H and the at least one reaction product has a formula selected from D-S—S—X, A-S—S—X, D-S—H, A-S—H, and salts thereof.

Embodiment 63. The method of embodiment 62, wherein detecting comprises at least one of: (a) observing dequenched fluorescence of the donor fluorophore in a reaction product having a formula selected from D-S—S—X, D-S—H, and salts thereof; (b) observing a change in the absorbance spectrum of the donor fluorophore in a reaction product having a formula selected from D-S—S—X, D-S—H, and salts thereof; and (c) observing a decrease in the fluorescence polarization of the donor fluorophore in a reaction product having a formula selected from D-S—S—X, D-S—H, and salts thereof.

Embodiment 64. The method of embodiment 62, comprising detecting a decrease in sensitized fluorescence of the acceptor fluorophore in a reaction product having a formula selected from A-S—S—X, A-S—H, and salts thereof.

Embodiment 65. The method of embodiment 52, wherein the at least one reaction product is detected in situ.

Embodiment 66. A method for detecting a thiol-containing compound, comprising: (A) reacting a reaction mixture to form at least one reaction product, the reaction mixture comprising: (i) the thiol-containing compound and (ii) a reagent comprising the compound of any of embodiments 38, 49, and 50; and (B) detecting the at least one reaction product.

Embodiment 67. The method of embodiment 66, wherein detecting the at least one reaction product is performed in real-time.

Embodiment 68. The method of embodiment 66, wherein detecting the at least one reaction product comprises at least one of: (a) observing dequenching of the donor fluorophore; (b) observing a change in the absorbance spectrum of the donor fluorophore; and (c) observing a decrease in the fluorescence polarization of the donor fluorophore.

Embodiment 69. The method of embodiment 66, wherein the thiol-containing compound includes glutathione.

Embodiment 70. The method of embodiment 66, wherein the thiol-containing compound includes homocysteine.

Embodiment 71. The method of embodiment 66, wherein the thiol-containing compound includes a cysteine-containing peptide.

Embodiment 72. The method of embodiment 66, wherein the thiol-containing compound includes ADPβS, GDPβS, or mixtures thereof.

Embodiment 73. The method of embodiment 66, wherein the thiol-containing compound has a formula X—S—H and the at least one reaction product has a formula selected from D-S—S—X, A-S—S—X, D-S—H, A-S—H, and salts thereof.

Embodiment 74. The method of embodiment 73, comprising detecting dequenched fluorescence of the donor fluorophore in a reaction product having a formula selected from D-S—S—X, D-S—H, and salts thereof.

Embodiment 75. The method of embodiment 66, wherein the at least one reaction product is detected in situ.

Embodiment 76. The method of embodiment 66, wherein the at least one reaction product is detected in tissue samples or biopsies.

Embodiment 77. The method of embodiment 66, wherein the at least one reaction product is detected in a cell.

Embodiment 78. The method of embodiment 77, further comprising calculating a redox potential for the cell.

Embodiment 79. A dithio compound having a formula $D-X^3$—S—S—$X^4$-A where "D" includes a donor fluorophore and "A" includes an acceptor non-fluorophore.

Embodiment 80. The dithio compound of embodiment 79, wherein $X^3$ and $X^4$ are the same or different and include one or more of the following groups: a $C_{1-18}$ alkyl group, an alkenyl group, an alkynyl group, and an aryl group.

Embodiment 81. A method for detecting a thiol-containing compound, comprising: (A) reacting a reaction mixture to form at least one reaction product, the reaction mixture comprising: (i) the thiol-containing compound and (ii) a reagent comprising the compound of embodiment 79 or 80; and (B) detecting the at least one reaction product.

Embodiment 82. The method of embodiment 81, wherein the thiol-containing compound includes glutathione.

The following examples are illustrative and not intended to limit the claimed subject matter.

EXAMPLES

Example 1

Synthesis of Fluorescein Isothiocyantate (FITC)/Rhodamine B Diamino Phenyl Disulfide Compound FITC-DAPS-RhoB Fluorescein isothiocyanate (FITC) was obtained from Sigma (Saint Louis, Mo.). Diamino phenyl disulfide, cystamine, rhodamine B and all organic solvents were obtained from Aldrich (Milwaukee, Wis.). The rhodamine sulfonyl chloride was obtained from Molecular Probes and Sigma. A stock solution of FITC-DAPS-RhoB was prepared in methanol containing 1% acetic acid. In the final 4 mL reaction mixture, the concentration of acid was 0.0025%.

Figure 3:
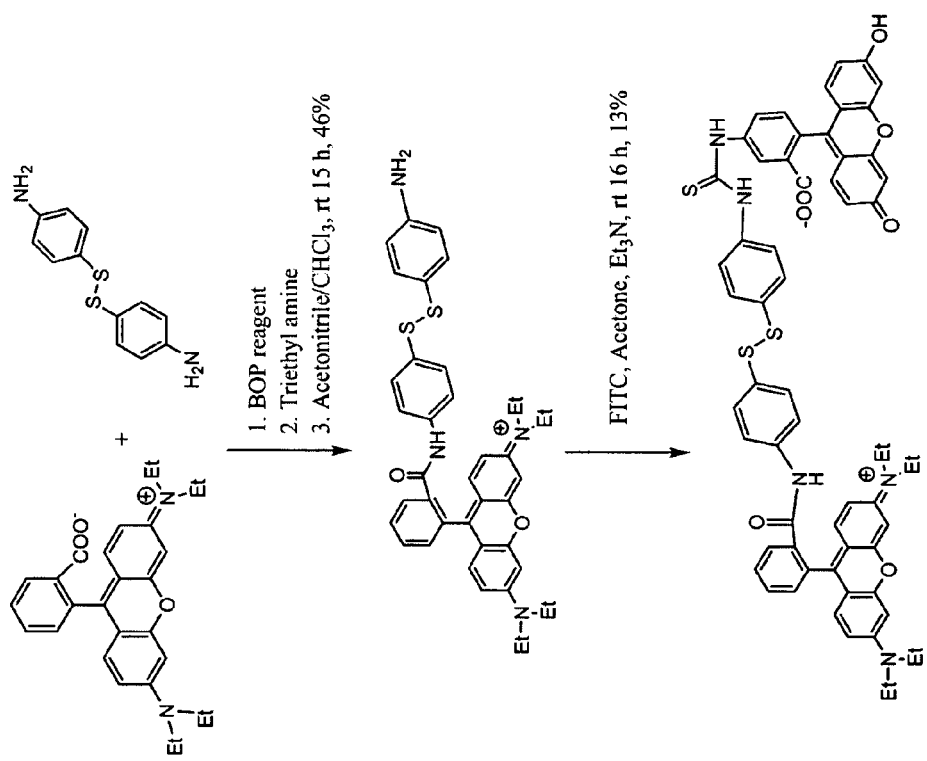
FIG. 3. Schematic representation of synthesis reaction for fluorescein/rhodamine diamino phenyl disulfide compound (F-DAPS-R).

Approximately 1 mmol of diamino phenyl disulfide ("DAPS") was dissolved in acetonitrile/chloroform mixture (4:1) (DAPS solution). Rhodamine B (0.3 mmol in acetonitrile) was added to the DAPS solution. (See FIG. 3). Reaction was initiated by adding 0.31 mmol BOP reagent and 20 mmol triethylamine and stirred for 15 h at room temperature. The amide was purified by silicagel (230-400μ) column chromatography using 20% ethyl acetate in hexane (% Yield: 46%).

The 0.1 mmol amide was reacted with 0.12 mmol FITC in acetone at room temperature for 16 h. The final FITC-DAPS-RhoB was purified by silicagel (230-400μ) column chromatography using 30% hexane in ethyl acetate and finally by preparative TLC (% Yield: 13%). All the above-described reactions were performed in the dark. All compounds were characterized by $^1$H-NMR, $^{13}$C-NMR and MALDI.

Example 2

Effect of pH on Emission of F-DAPS-R Dithio Compound

Figure 4:
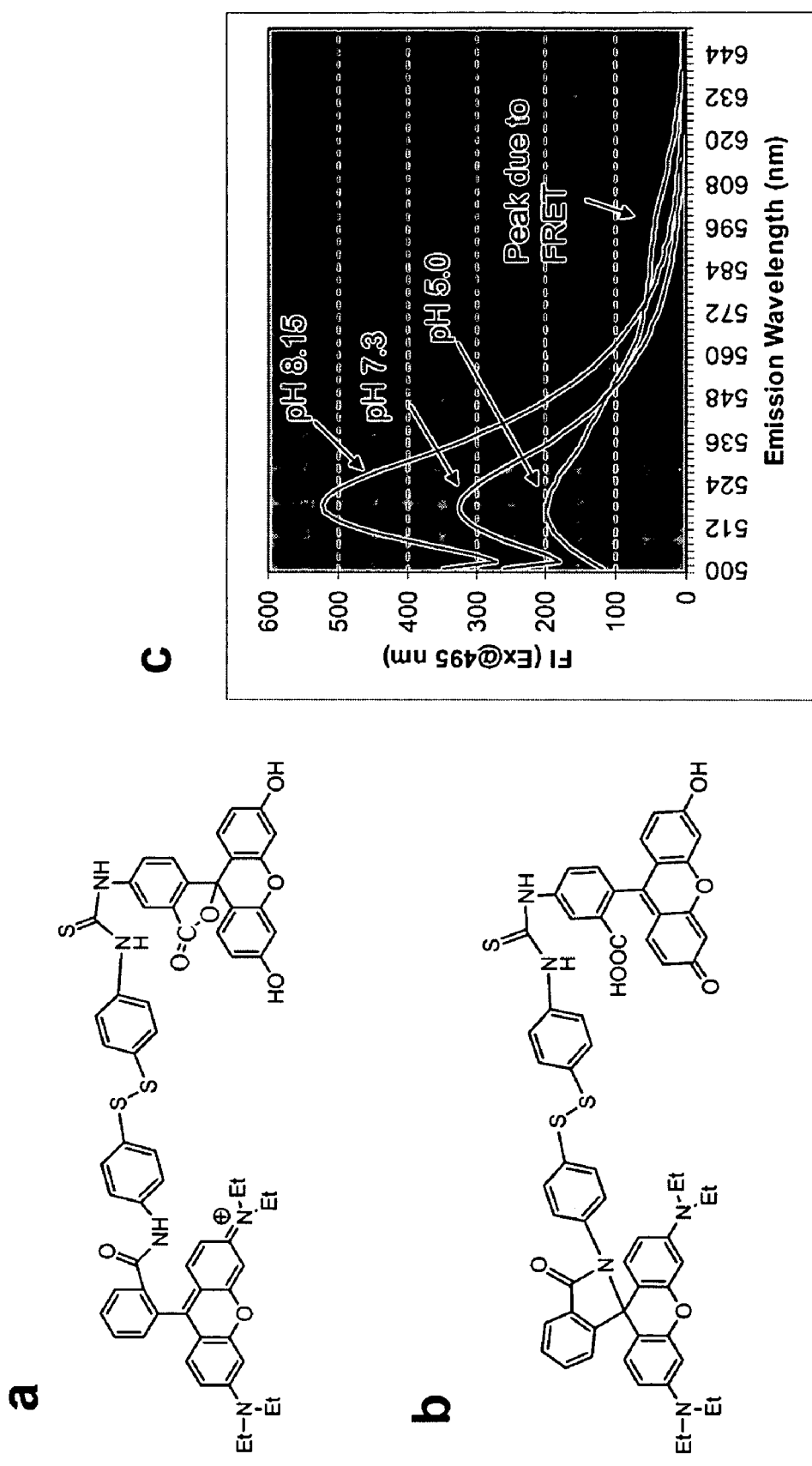
FIG. 4. Representation of dithio compound F-DAPS-R, (a) at acidic pH, and (b) basic pH. (c) Fluorescence emission spectra (Ex@495 nm) of F-DAPS-R at different pHs.
Figure 5:
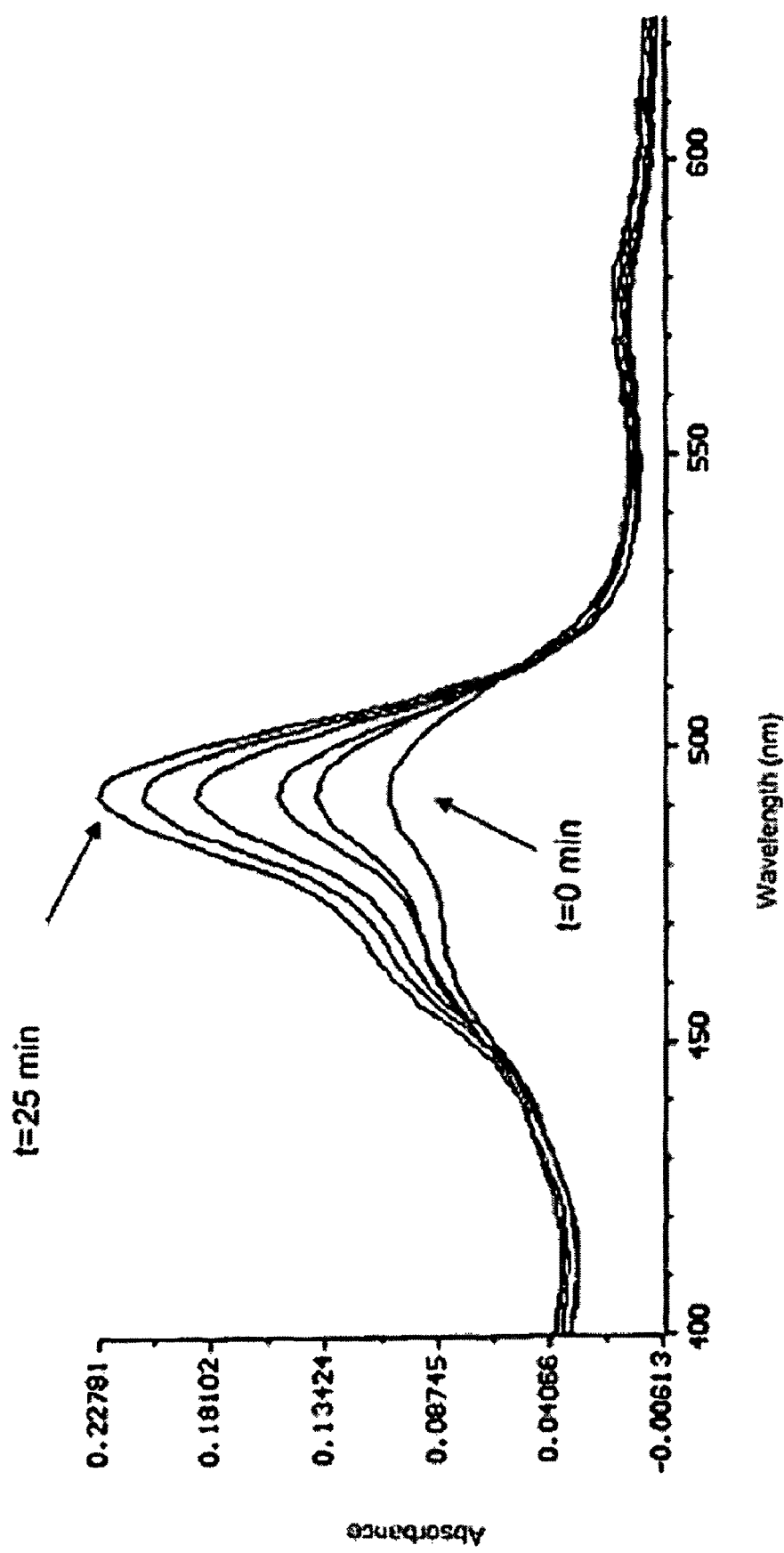
FIG. 5. Thiol-based reduction of F-DAPS-R in 2.5 mM DTT, as a function of time (t). Spectra were acquired every five minutes for 25 minutes, then overlaid.
Figure 6:
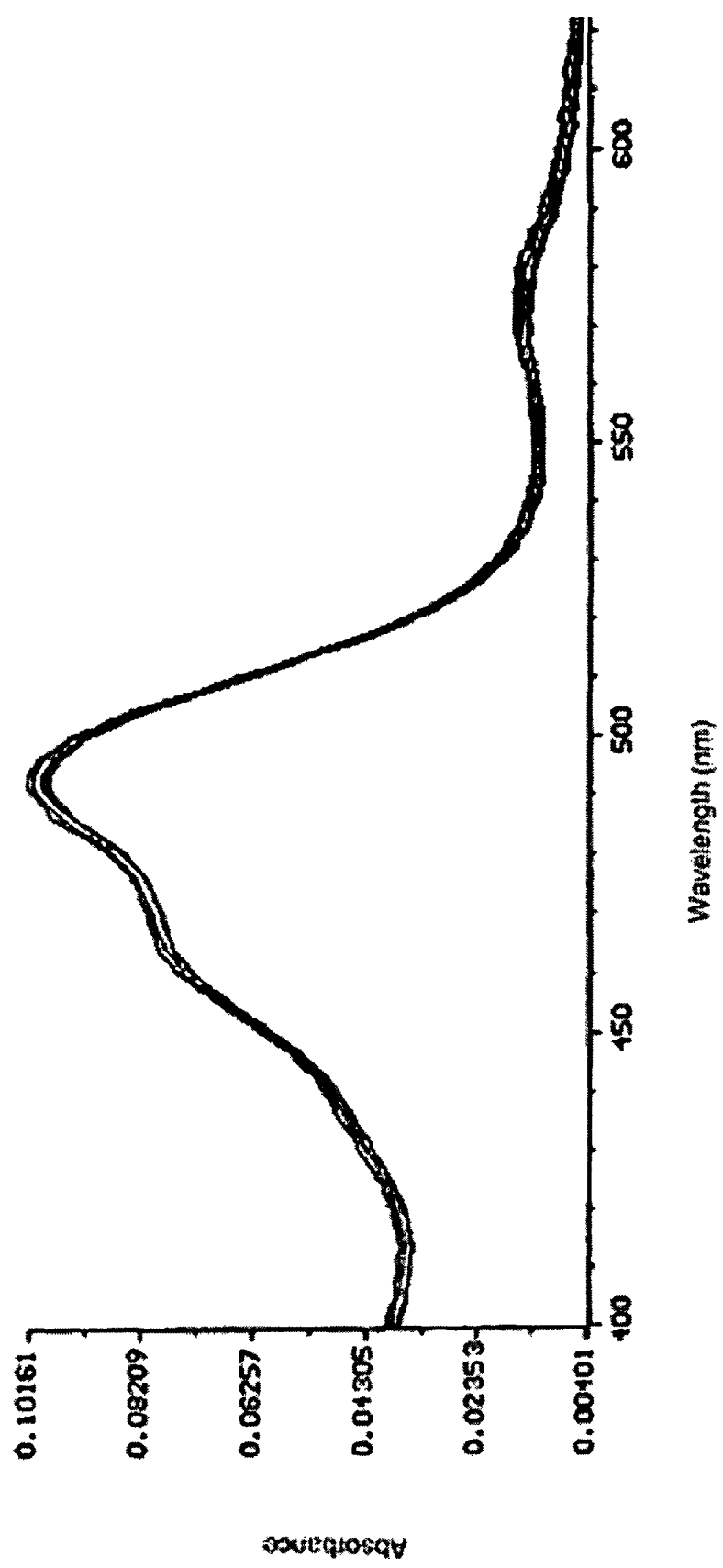
FIG. 6. Thiol-based reduction of F-DAPS-R without DTT, as a function of time (t). Spectra were acquired every five minutes for 25 minutes, then overlaid.
Figure 7:
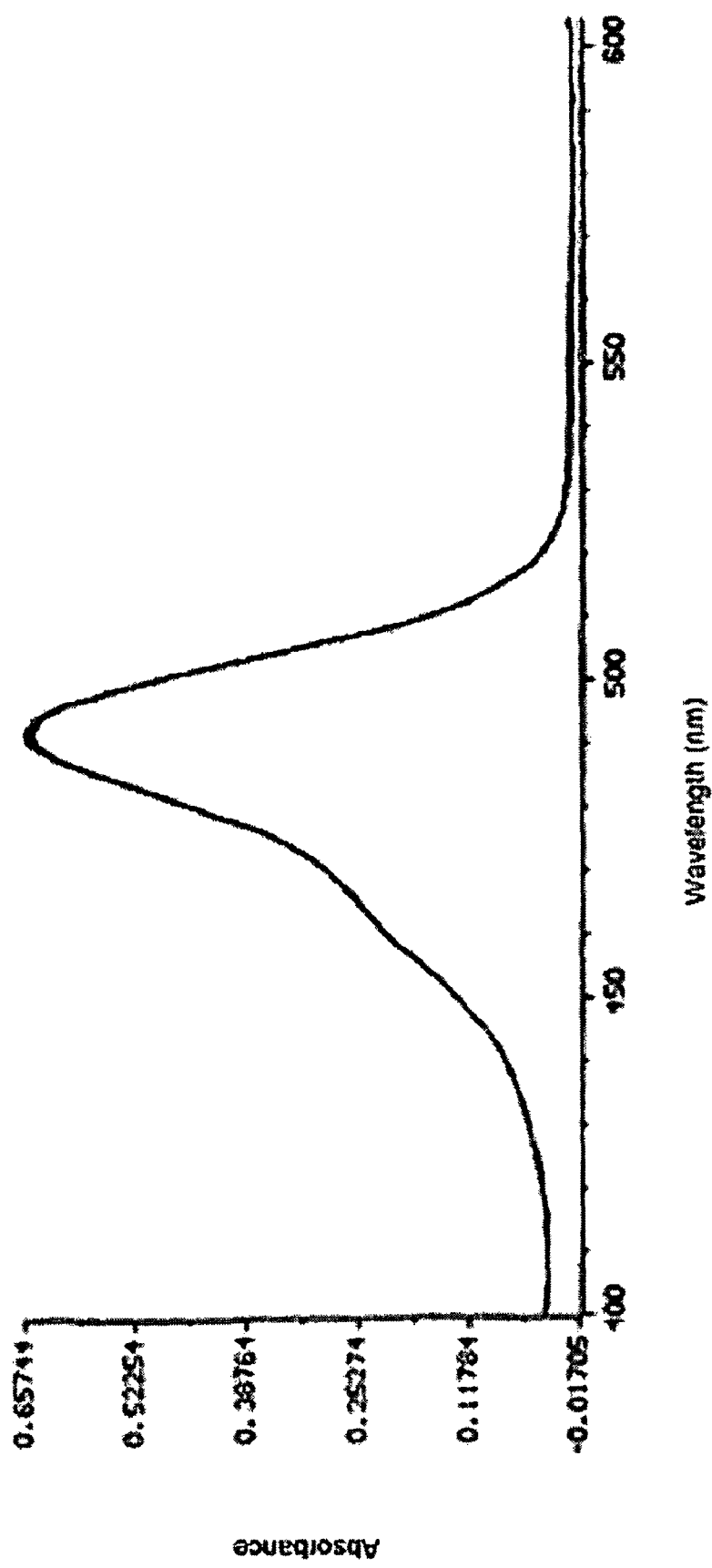
FIG. 7. Spectra for 5 μM FITC in 2.5 mM DTT.
Figure 8:
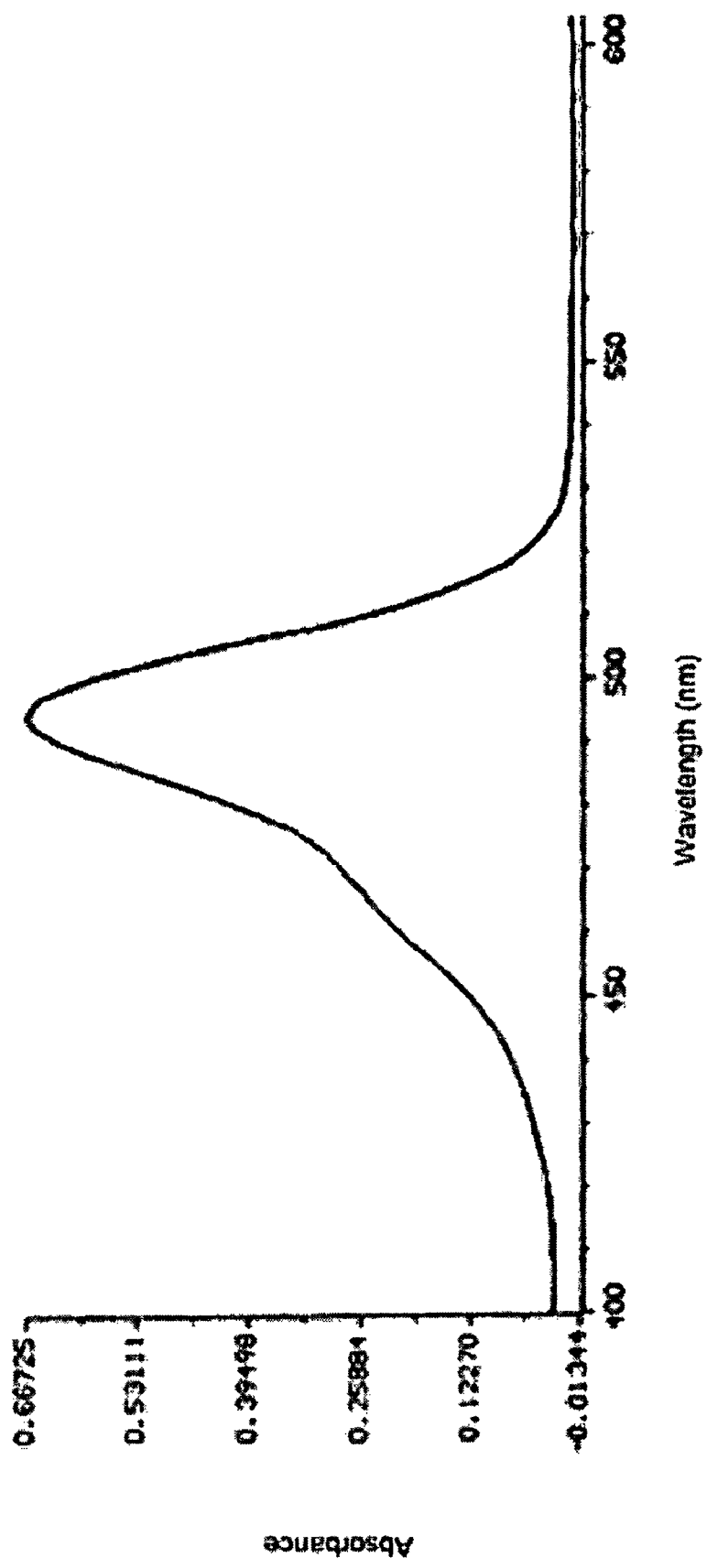
FIG. 8. Spectra for 5 μM FITC without DTT.

The effect of pH (5.0, 7.3, and 8.15) on the emission spectrum of F-DAPS-R (Ex@495 m) was analyzed. (See FIG. 4.) A main peak was observed at approximately 520 nm, apparently due to fluorescence emission from the donor. The peak observed at approximately 595 nm is due apparently to emission from the acceptor due to FRET.

Example 3

Kinetics of Thiol-Based Reduction of F-DAPS-R

Figure 9:
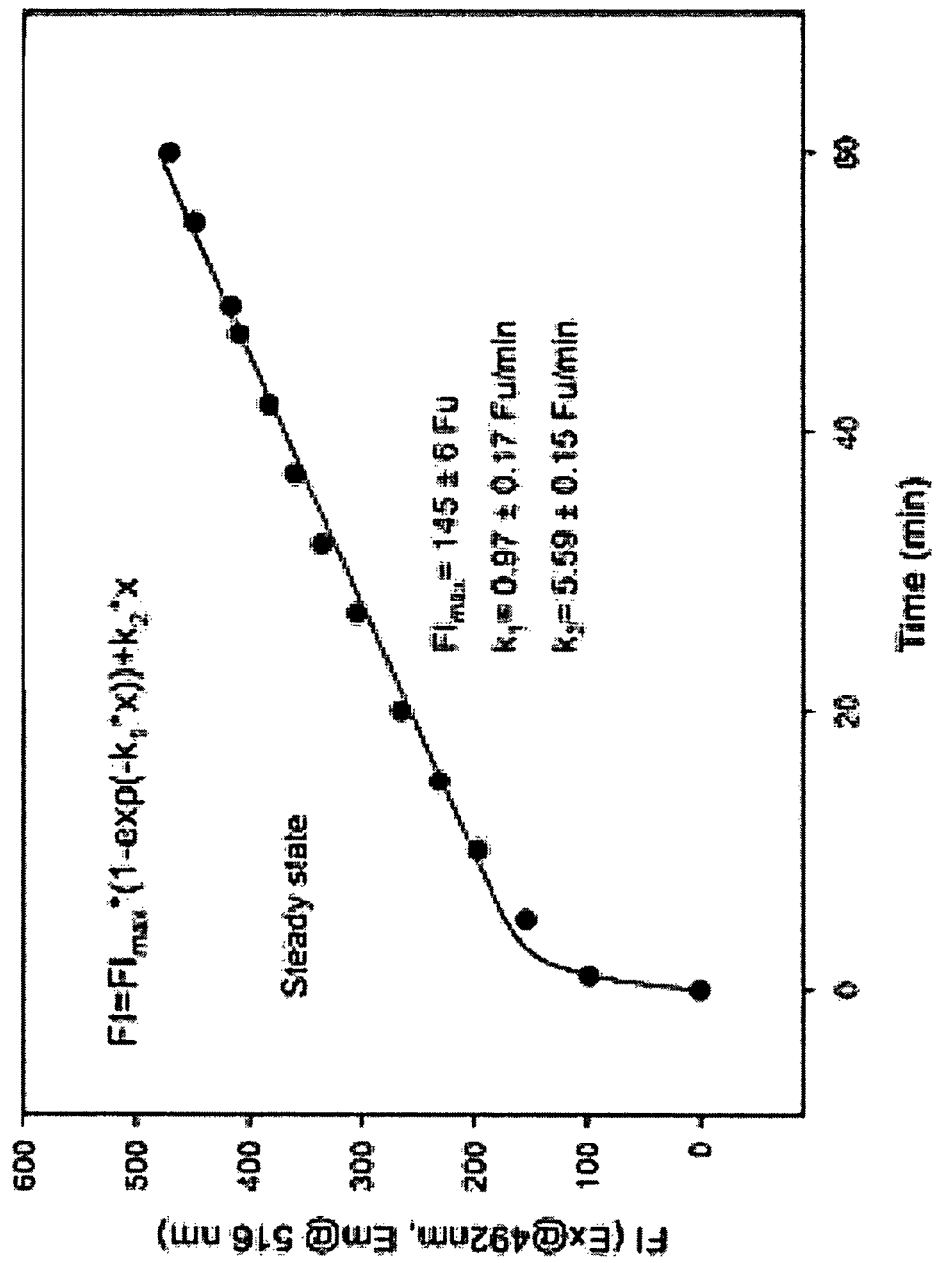
FIG. 9. Plot and fit of fluorescence emission as a function of time for 5 μM F-DAPS-R and 2.5 mM DTT in pH 7.0 buffer.
Figure 10:
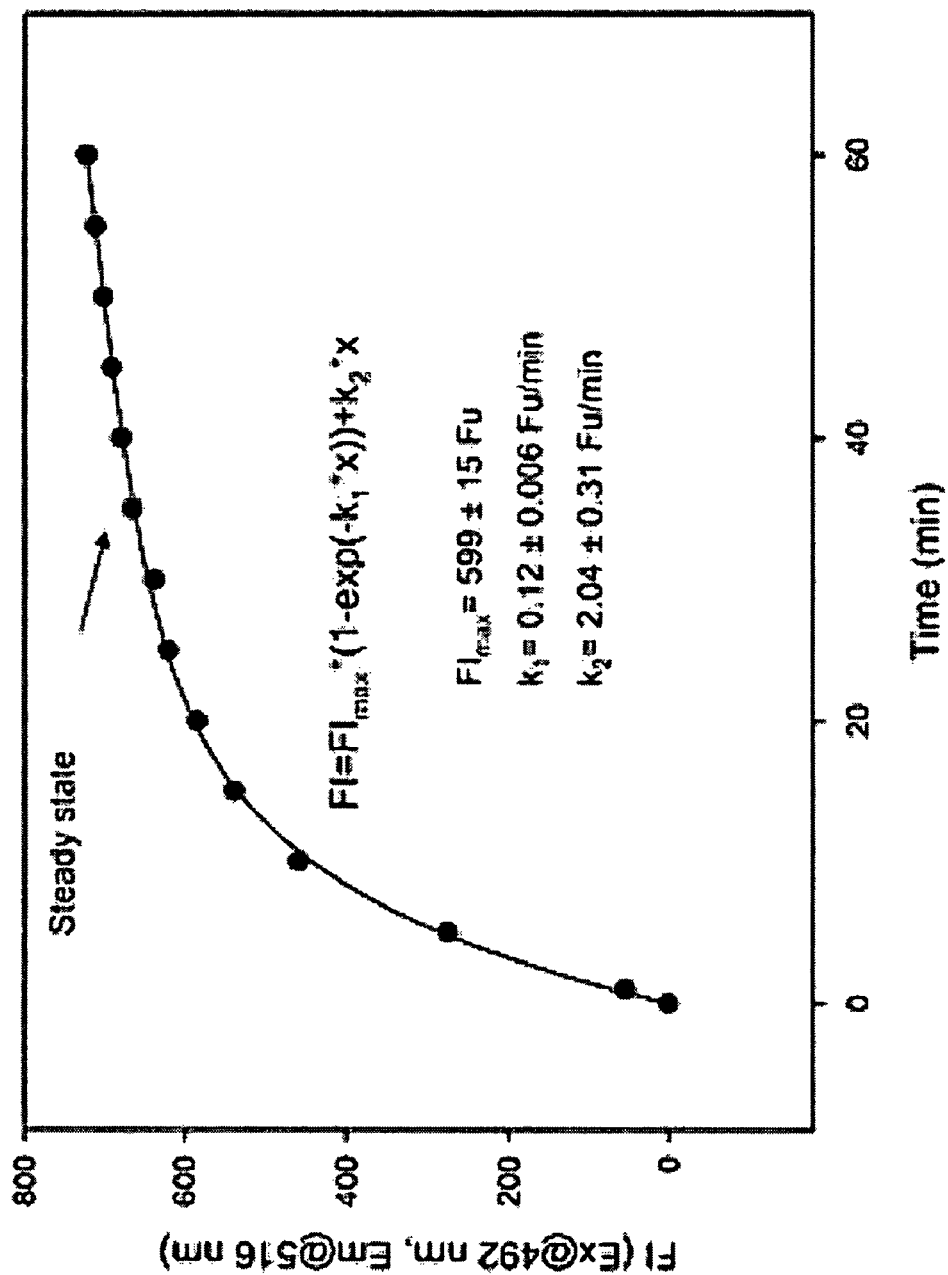
FIG. 10. Plot and fit of fluorescence emission as a function of time for 5 μM F-DAPS-R and 2.5 mM DTT in pH 8.15 buffer.

The effect of adding 2.5 mM DTT to F-DAPS-R (5 μM) was analyzed over time in comparison to F-DAPS-R (no DTT), FITC (with DTT), and FITC (no DTT). (See FIGS. 5-8). Absorption spectra of the donor as a function of time are shown, including an increase in absorption at approximately 495 nm, apparently due to reduction of the dithio compound. Fluorescence emission as a function of time is shown in FIGS. 9 and 10, which demonstrated dequenching at an emission of approximately 495 nm, apparently due to reduction of the dithio compound, at two pH values.

Example 4

Reaction of Glutathione and F-DAPS-R

Figure 11:
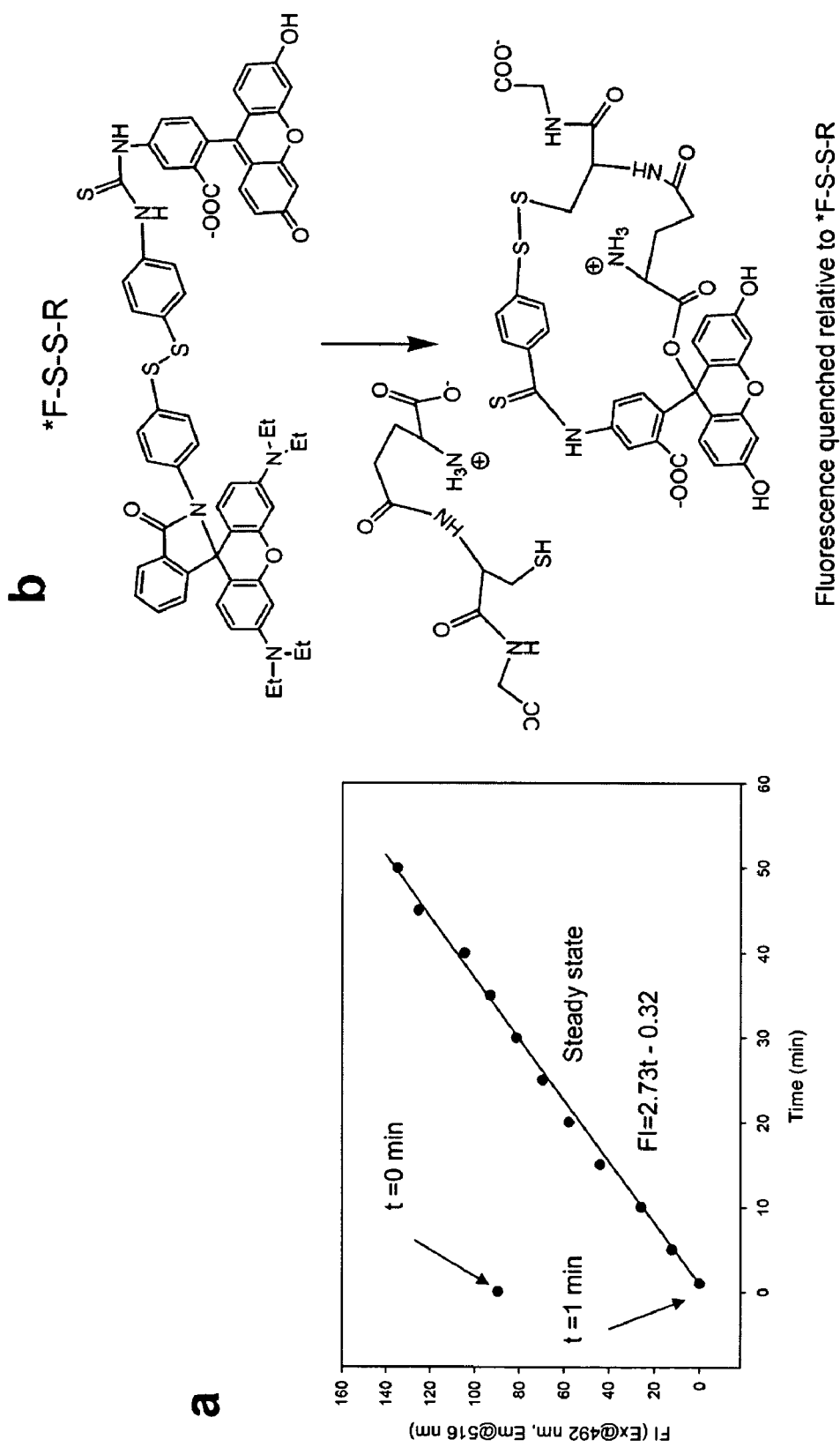
FIG. 11. Reaction of F-DAPS-R and glutathione: (a) 2.5 mM glutathione was added to 5 μM F-DAPS-R and fluorescence emission was monitored versus time; (b) possible intermediate formed for t=0-1 min.

Glutathione (2.5 mM) was added to F-DAPS-R (5 μM). Fluorescence emission was analyzed over time (0-50 minutes), and dequenching was observed. (See FIG. 11).

Example 5

Selective Reaction of ADPβS Versus ATPβS and F-DAPS-R and Use in Kinase Coupled Assay ADPβS (or ATPβS), 500 μM, was added to F-DAPS-R (1 μM) in 96 well plates. Fluorescence emission from the donor was analyzed (Ex: 485 nm, Em: 520 nm) over time (0-45 minutes), using a POLARstar Galaxy FP plate reader. (See FIG. 12). Dequenching was observed for the reaction with ADPβS, while no reaction was observed with ATPβS. A comparison of a thiol-based coupled kinase assay and the commonly used pyruvate kinase/lactate dehydrogenase-coupled kinase assay (PK/LDH assay) is shown in FIG. 13. Change in absorption properties of the donor fluorophore, upon reduction of the dithio group, are indicated in FIG. 13D.

Example 6

Uptake of F-DAPS-R in *E. coli* Cells

Dithiol reagents were added to growing *E. coli* cells at 0.6 absorbance units ($OD_{600}$) and fluorescence measurements taken at different times. (See FIG. 16.) Dithiol reagents included rhodamine B/FITC linked with DAPS or cystamine (Rh-DAPS-FITC and Rh-CYST-FITC, respectively). After the reagent was added to the cells, 1 mL of growing cells were sampled, centrifuged and washed three times with 1 mL of 100 mM Tris buffer (pH 8.15). After each washing, the cells were centrifuged and the supernatant was decanted. Fluorescence (emission at 520 nm after excitation of the donor at 489 nm) was recorded by re-suspending cells in 4 mL of pH 8.15 Tris buffer. Results were the average of five replicates, and the standard deviation of all readings was less than 10%. Fluorescence signal for uptake into *E. coli* cells deficient in synthesis of thioredoxin reductase ("Origami cells") was observed to be much less for both reagents.

Example 7

Use of Dithio Reagents for Detecting Thiol-Containing Compounds In Situ

Thiol levels were monitored in tissues in situ. Zebrafish embryos were labeled with two forms of the F—S—S—R reagent (i.e., F-DAPS-R and F-CYST-R). Localization of labeling was monitored using fluorescence microscopy. Zebrafish were exposed to the reagent by adding the reagent externally in growth media or via microinjection through the zebrafish chorion. By either method, the chorion was labeled, suggesting that the chorion includes thiol-containing compounds (e.g., thiol-containing proteins). (See FIG. 17).

Example 8

Use of Dithio Reagents to Determine Redox Potential

Glutathione levels can be used to estimate redox state of cell. For example, the GSH/GSSG ratio may be estimated based on relative fluorescence measurements, as determined by calculating the ratio of F—S—S—R relative to F—S⁻ or R—S⁻. The estimated GSH/GSSG ratio may be used to calculate redox potential, based on the pH dependent Nernst equation. First, reduction potential may be determined in vitro by reacting F—S—S—R and thiol reductants (e.g., DTT, GSH). The determined reduction potential then may be used to calculate a redox potential in vivo. Ratios of F—S—S—R to F—S⁻ or R—S⁻ may be calculated using the fluorescent properties of each of these compounds. Measurement of the redox state of a cell or tissue may be used as a diagnostic measurement of cell health or disease (i.e., as a "biomarker").

Example 9

Synthesis of 2-(6-Hydroxy-3-oxo-3H-xanthen-9-yl)-4-[4-(4-methyl-2-oxo-2H-chromen-7-yldisulfanyl)-thiobenzoylamino]-benzoic acid

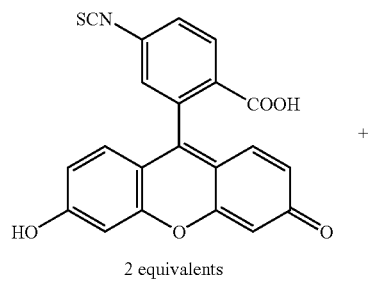

2 equivalents

+

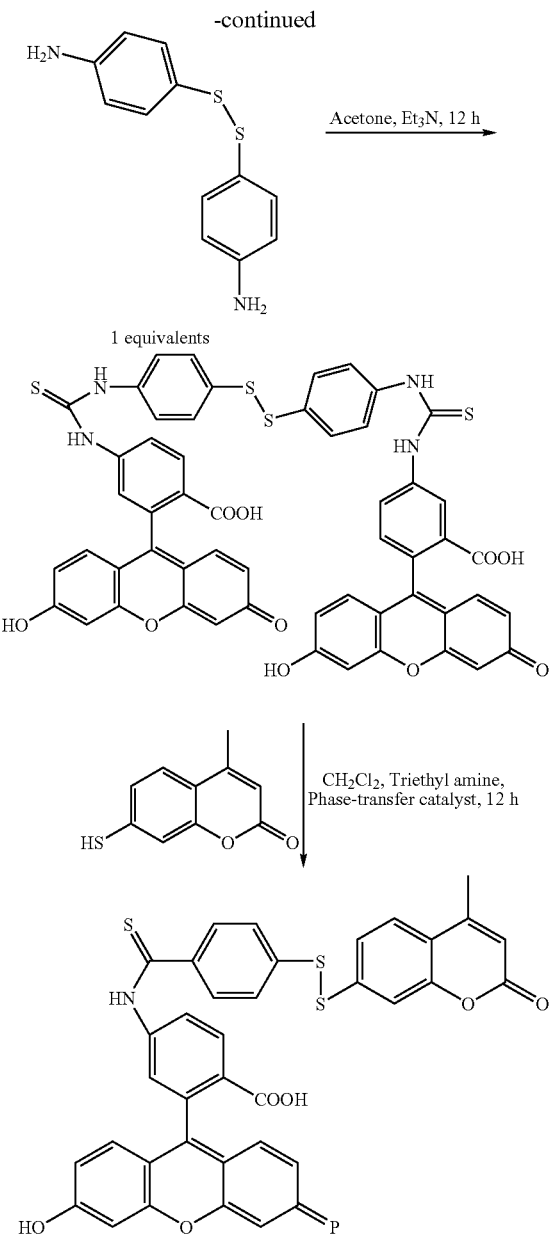

Procedure: Fluorescein isothiocyanate (isomer 1, 2 mmol) and diaminophenyldisulphide (1 mmol) and triethyl amine (8 mmol) were dissolved in 25 mL of acetone. The red color solution was stirred for 15 min. A reddish precipitate was observed and the reaction was continued for another 12 hours. The reaction mixture was concentrated and purified using flash chromatography. Silicagel (240-400 mesh, 30 g) was loaded on a glass column using hexane. The reaction mixture was dissolved in a minimum amount of dichloromethane and loaded on to the silicagel and chromatographed using a gradient of ethyl acetate and hexane. Appropriate fractions were pooled and concentrated. The obtained difluorescein substituted disulphide (0.5 mmol) was reacted with 7-mercapto 4-methyl coumarin (3 mmol) in dichloromethane (10 mL) in the presence of benzyl tributyl ammonium bromide (phase transfer catalyst, 0.01 mol) for 12 hours. The resultant product, 2-(6-Hydroxy-3-oxo-3H-xanthen-9-yl)-4-[4-(4-methyl-2-oxo-2H-chromen-7-yldisulfanyl)-thiobenzoylamino]-benzoic acid, was purified by flash chromotagraphy. Silicagel (240-400 mesh, 30 g) was loaded on a glass column using hexane. Reaction mixture was dissolved in a minimum amount of dichloromethane and loaded on to the silicagel and chromatographed using a gradient of ethyl acetate and hexane. Appropriate fractions were pooled and concentrated. MALDI, m/z calc'd=689.78, observed=689.29.

Example 10

Synthesis of {9-[2-(4-{3-[4-(4-{3-[4-Carboxy-3-(6-hydroxy-3-oxo-3H-xanthen-9-yl)-phenyl]-thioureido}-phenyldisulfanyl)-phenylcarbamoyl]-propionyl}-piperazine-1-carbonyl)-phenyl]-6-diethylamino-xanthen-3-ylidene}-diethyl-ammonium

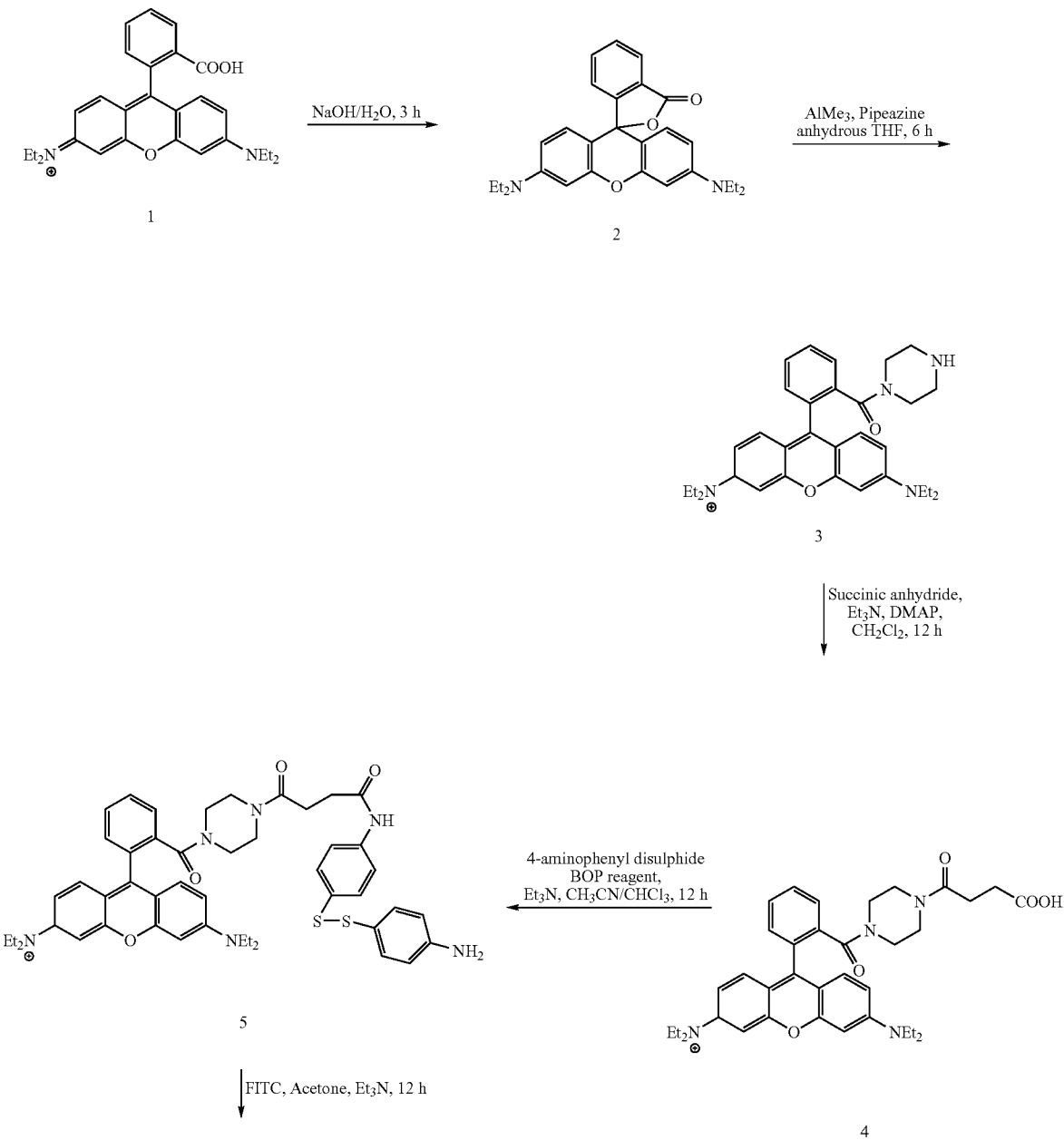

-continued

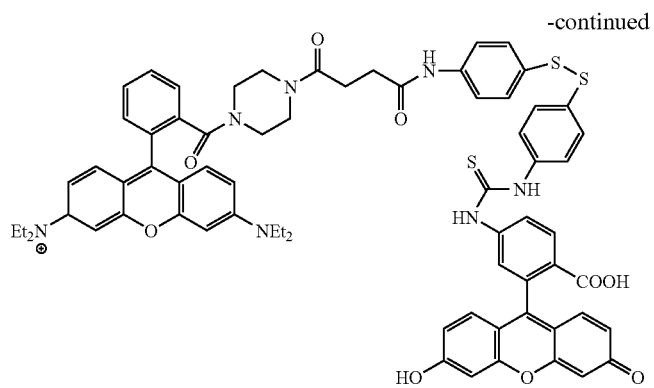

6

Procedure:

Synthesis of Rhodamine B base (2). Rhodamine B (1, 0.69 mmol) was dissolved and partitioned between aqueous 1 M NaOH and EtOAc. After isolation of the organic layer, the aqueous layer was extracted with two additional portions of EtOAc. The combined organic layers were then washed with NaOH and brine. The resulting organic solution was dried over $Na_2SO_4$, filtered, and concentrated under reduced pressure to yield product as a pink foam (93%): $^1$H NMR (300 MHz, $CD_3OD$): δ 1.26-1.31 (t, 12, J=6.9), 3.61-3.68 (q, 8, J=6.9), 6.90-6.91 (d, 2, J=2.4), 6.96-7.00 (dd, 2, J=2.7, 9.6), 7.23-7.29 (m, 3), 7.57-7.67 (m, 2), 8.07-8.09 (m, 1).

Synthesis of Rhodamine B piperazine amide (3). A 2.0 M solution of trimethyl aluminum in toluene (4.5 mmol) was added dropwise to a solution of piperazine (9.1 mmol) in 35 mL of $CH_2Cl_2$ at room temperature. After one hour of stirring a white precipitate was observed. A solution of rhodamine B base (2, 2.3 mmol) in 20 mL of $CH_2Cl_2$ was added drop wise to the heterogeneous solution. Gas evolution was observed during the addition period. After stirring at reflux for 12 h, a 0.1 M aqueous solution of HCl was added drop wise until gas evolution ceased. The heterogeneous solution was filtered and the retained solids were rinsed with $CH_2Cl_2$ and a 4:1 $CH_2Cl_2$/MeOH solution. The combined filtrate was concentrated and the residue was dissolved in $CH_2Cl_2$, filtered to remove insoluble salts, and concentrated again. The resulting glassy solid was then partitioned between dilute aqueous $NaHCO_3$ and EtOAc. After isolation, the aqueous layer was washed with 3 additional portions of EtOAc to remove residual starting material. The retained aqueous layer was saturated with NaCl, acidified with 1 M aqueous HCl, and then extracted with multiple portions of 2:1 iPrOH/$CH_2Cl_2$, until a faint pink color persisted. The combined organic layers were then dried over $Na_2SO_4$, filtered, and concentrated under reduced pressure. The glassy purple solid was dissolved in a minimal amount of MeOH and precipitated by drop wise addition to a large volume of $Et_2O$. The product was collected by filtration as a dark purple solid. mp 219-220° C. IR: 1630 cm$^{-1}$. $^1$H NMR (500 MHz, $CD_3OD$): δ 1.28-1.33 (t, 12, J=7.5), 3.12 (br s, 4), 3.64-3.74 (m, 12), 6.97-6.98 (d, 2, J=2.5), 7.09-7.11 (dd, 2, J=2.5, 10.0), 7.26-7.27 (d, 2, J=9.5), 7.51-7.54 (m, 1), 7.76-7.80 (m, 3). $^{13}$C NMR (300 MHz, $CD_3OD$) δ 13.07, 44.34, 45.59, 47.05, 97.51, 114.87, 115.67, 129.04, 131.50, 131.63, 131.97, 132.54, 133.08, 135.75, 156.82, 157.28, 159.32, 169.48. MALDI, m/z calcd 510.31 found 510.29.

Synthesis of Rhodamine B 4-(3-Carboxypropionyl)piperazine amide (4). Triethylamine (4 mmol) was added to a stirred solution of 3 (0.3 mmol), succinic anhydride (0.4 mmol), and DMAP (0.4 mmol) in $CH_2Cl_2$ (5 mL). After stirring at room temperature for 12 h, the reaction solution was partitioned between EtOAc and 1 M aqueous $K_2CO_3$. The aqueous layer was washed with 3 additional portions of EtOAc. Sodium chloride was added to the isolated aqueous layer until saturation was achieved and the solution was then extracted with 2:1 isopropanol/$CH_2Cl_2$. The organic layer was dried over $Na_2SO_4$, and concentrated under reduced pressure. The resulting solid was dissolved in $CHCl_3$ and filtered to remove insoluble salts. Upon concentration, the product was obtained as a dark solid. mp: 166-168° C. IR: 1720 cm$^{-1}$. $^1$H NMR (300 MHz, $CD_3OD$) δ 1.28-1.32 (t, 12H, J=6.8), 2.54 (br s, 2H), 2.59 (br s, 2H), 3.41 (br, s 8H), 3.66-3.71 (q, 8H, J=7.2), 6.96-6.97 (d, 2H, J=2.0), 7.09 (br s, 2H), 7.27-7.29 (d, 2H, J=9.6), 7.52-7.53 (m, 1H), 7.69-7.71 (m, 1H), 7.76-7.78 (m, 2H). $^{13}$C NMR (75 MHz, $CD_3OD$) δ 13.03, 28.94, 30.33, 40.40, 43.08, 47.05, 50.00, 97.49, 114.95, 115.57, 129.07, 131.42, 131.90, 132.41, 133.29, 136.66, 140.14, 157.12, 157.29, 169.62, 172.82, 176.67. MALDI m/z calcd 611.32, found 611.32.

Synthesis of {9-[2-(4-{3-[4-(4-Amino-phenyldisulfanyl)-phenylcarbamoyl]-propionyl}-piperazine-1-carbonyl)-phenyl]-6-diethylamino-xanthen-3-ylidene}-diethyl-ammonium (5): 1 mmol of diaminophenyl disulfide dissolved in a 4:1 acetonitrile/chloroform mixture, to which 0.3 mmol Rhodamine B 4-(3-Carboxypropionyl)piperazine amide (4) in acetonitrile was added. Reaction was initiated by the addition of 0.31 mmol BOP (benzotriazol-1-(yloxy)tris(dimethylamino)phosphonium hexafluorophosphate) reagent and 20 mmol triethylamine and stirred for 12 h at room temperature. The amide (5) was purified by silica gel (230-400 ii) column chromatography using 90% ethyl acetate in hexane (yield=37%). MALDI m/z calcd 841.36, found 841.32

Synthesis of {9-[2-(4-{3-[4-(4-{3-[4-Carboxy-3-(6-hydroxy-3-oxo-3H-xanthen-9-yl)-phenyl]-thioureido}-phenyldisulfanyl)-phenylcarbamoyl]-propionyl}-piperazine-1-carbonyl)-phenyl]-6-diethylamino-xanthen-3-ylidene}-diethyl-ammonium (6): The 0.1 mmol amide (5) was reacted with 0.12 mmol fluorescein 5-isothiocyanate (FITC) in acetone at room temperature for 12 h. The final probe (6) was purified by silica gel (230-400μ) column chromatography using 80% hexane in ethyl acetate and then by preparative thin-layer chromatography. MALDI m/z calcd=1230.39; observed=1230.72

By using the synthetic procedures described in Examples 9 and 10, a number of DSSA-type compounds may be synthesized as provided in Examples 11-22.

Example 11

Synthesis of (9-{2-[4-(3-{2-[3-Carboxy-4-(6-hydroxy-3-oxo-3H-xanthen-9-yl)-phenylcarbamoyl]-ethyldisulfanyl}-propionyl)-piperazine-1-carbonyl]-phenyl}-6-diethylamino-xanthen-3-ylidene)-diethyl-ammonium The synthetic procedure described in Example 10 is modified in the scheme below:

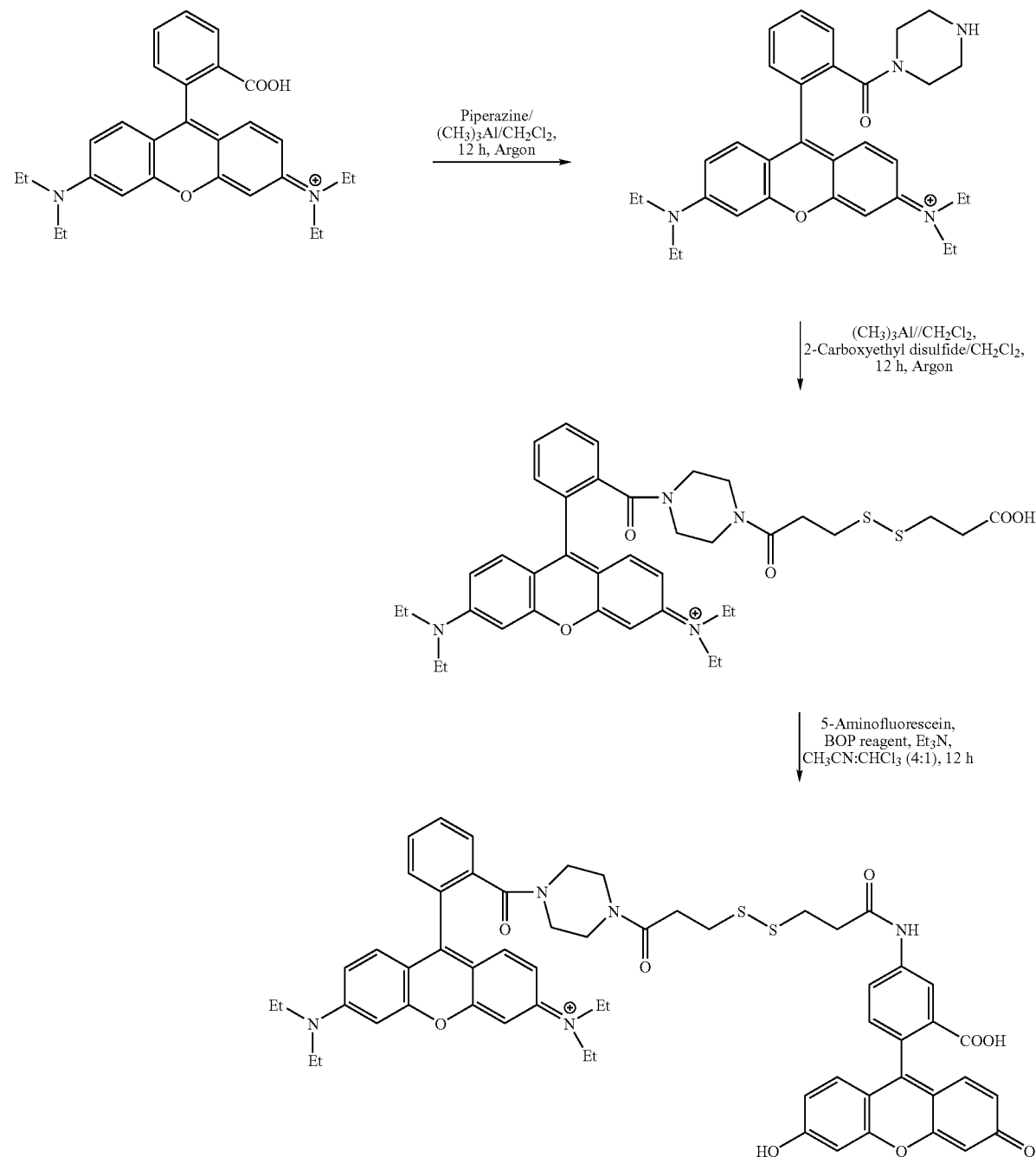

Example 12
Synthesis of (9-{2-[4-(2-{2-[3-Carboxy-4-(6-hydroxy-3-oxo-3H-xanthen-9-yl)-phenylcarbamoyl]-phenyldisulfanyl}-benzoyl)-piperazine-1-carbonyl]-phenyl}-6-diethylamino-xanthen-3-ylidene)-diethylammonium
The synthetic procedure described in Example 10 is modified in the scheme below:
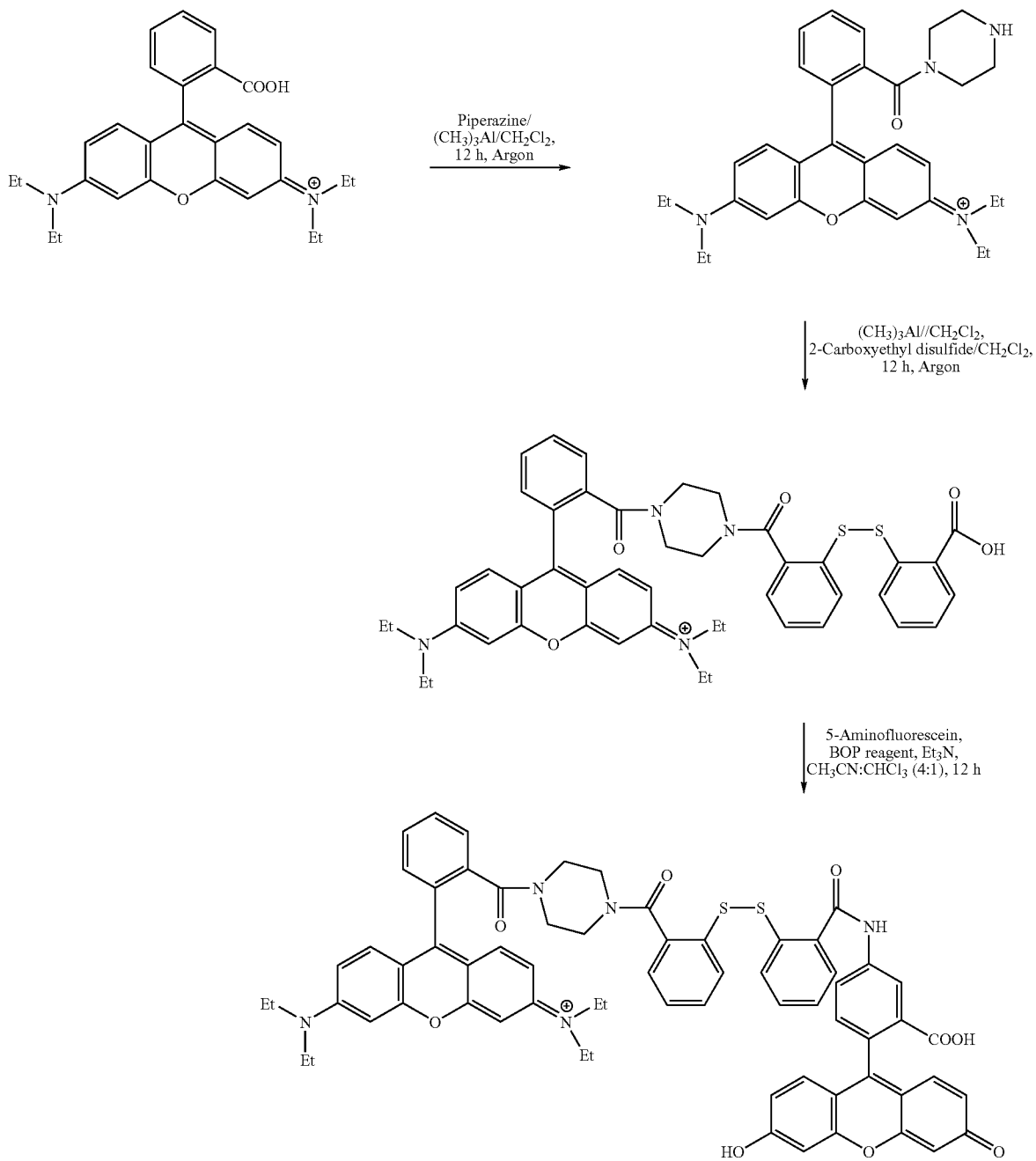

Example 13

Synthesis of 2-(6-Hydroxy-3-oxo-3H-xanthen-9-yl)-5-{2-[2-(2-oxo-2H-chromen-6-ylcarbamoyl)-phenyldisulfanyl]-benzoylamino}-benzoic acid The synthetic procedure described in Example 10 is modified in the scheme below:

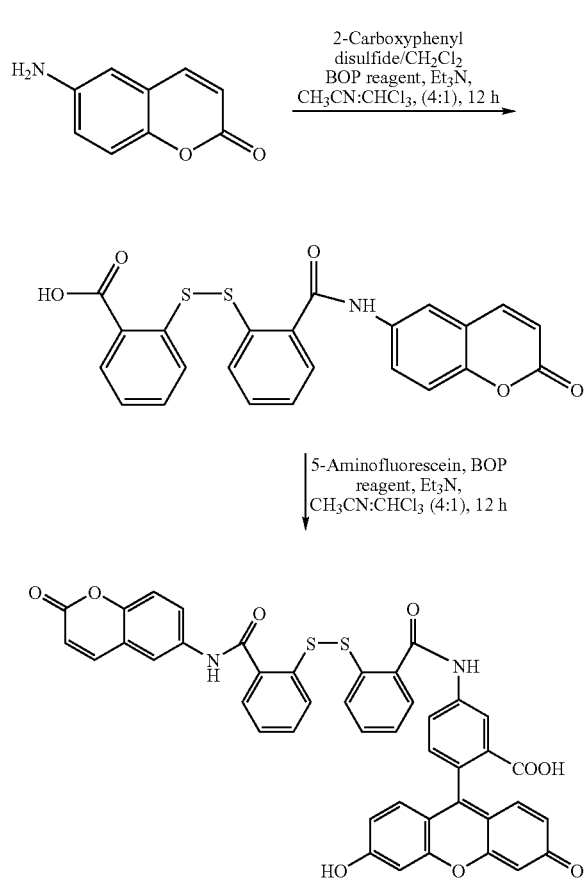

Example 14

Synthesis of 2-(6-Hydroxy-3-oxo-3H-xanthen-9-yl)-5-{3-[2-(2-oxo-2H-chromen-6-ylcarbamoyl)-ethyldisulfanyl]-propionylamino}-benzoic acid The synthetic procedure described in Example 10 is modified in the scheme below:

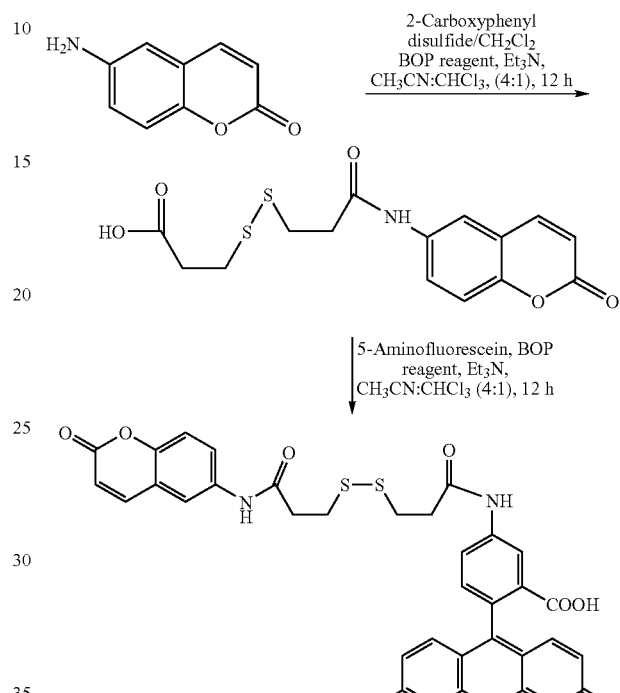

Example 15

Synthesis of (6-Diethylamino-9-{2-[4-(3-{2-[4-(6-hydroxy-3-oxo-3H-xanthen-9-yl)-3-trifluoromethyl-phenylcarbamoyl]-ethyldisulfanyl}-propionyl)-piperazine-1-carbonyl]-phenyl}-xanthen-3-ylidene)-diethyl-ammonium The synthetic procedure described in Example 10 is modified in the scheme below:

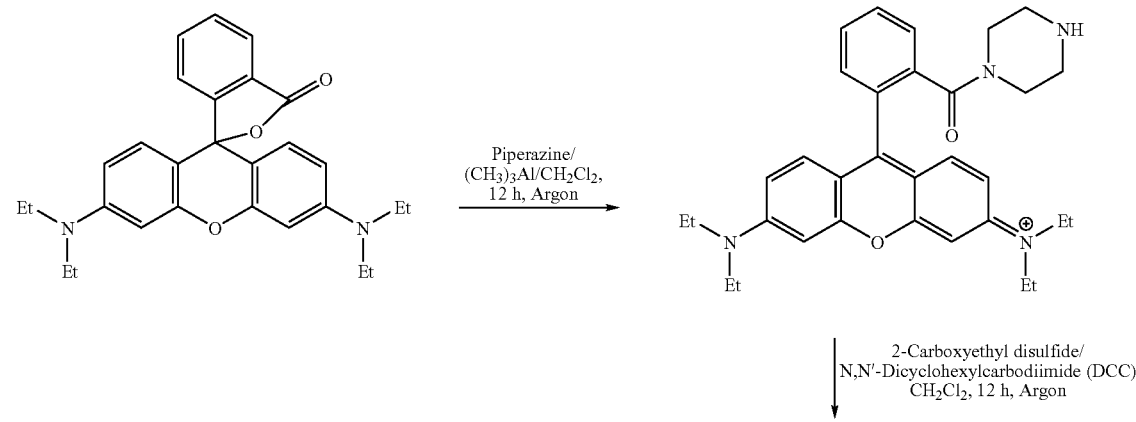

-continued
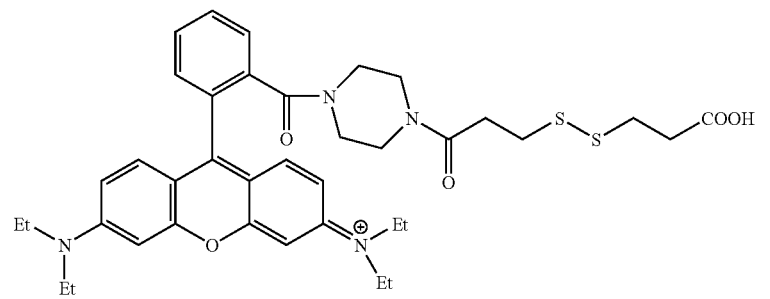
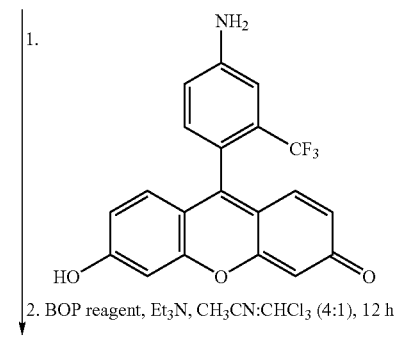
2. BOP reagent, Et₃N, CH₃CN:CHCl₃ (4:1), 12 h
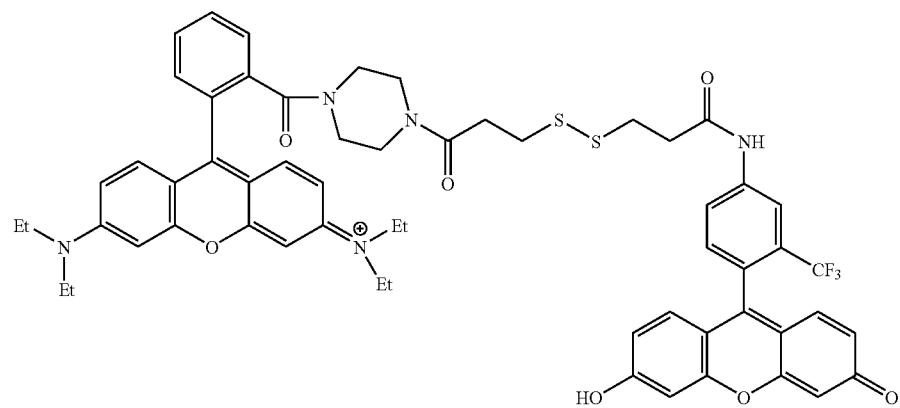

Example 16
(6-Diethylamino-9-{2-[4-(2-{2-[4-(6-hydroxy-3-oxo-3H-xanthen-9-yl)-3-trifluoromethyl-phenylcarbamoyl]-phenyldisulfanyl}-benzoyl)-piperazine-1-carbonyl]-phenyl}-xanthen-3-ylidene)-diethylammonium
The synthetic procedure described in Example 10 is modified in the scheme below:
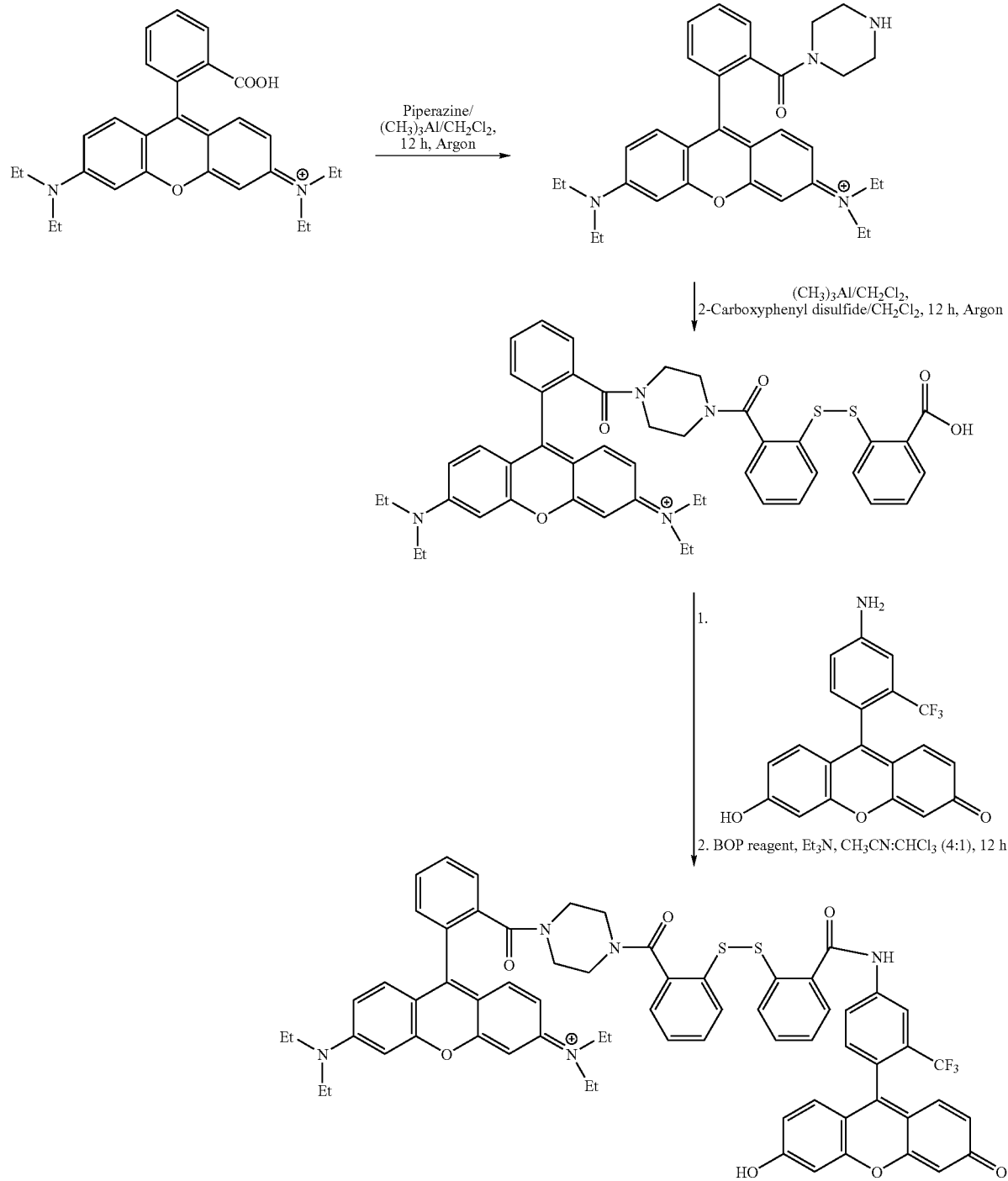

Example 17

[4-(2-{2-[4-(6-hydroxy-3-oxo-3H-xanthen-9-yl)-3-trifluoromethyl-phenylcarbamoyl]-phenyldisulfanyl}-benzoyl)2-[2-(2-Oxo-2H-chromen-6-ylcarbamoyl)-phenyldisulfanyl]-propionamide The synthetic procedure described in Example 10 is modified in the scheme below:

Example 18

N-[4-(6-Hydroxy-3-oxo-3H-xanthen-9-yl)-3-trifluoromethyl-phenyl]-3-[2-(2-oxo-2H-chromen-6-ylcarbamoyl)-ethyldisulfanyl]-propionamide The synthetic procedure described in Example 10 is modified in the scheme below:

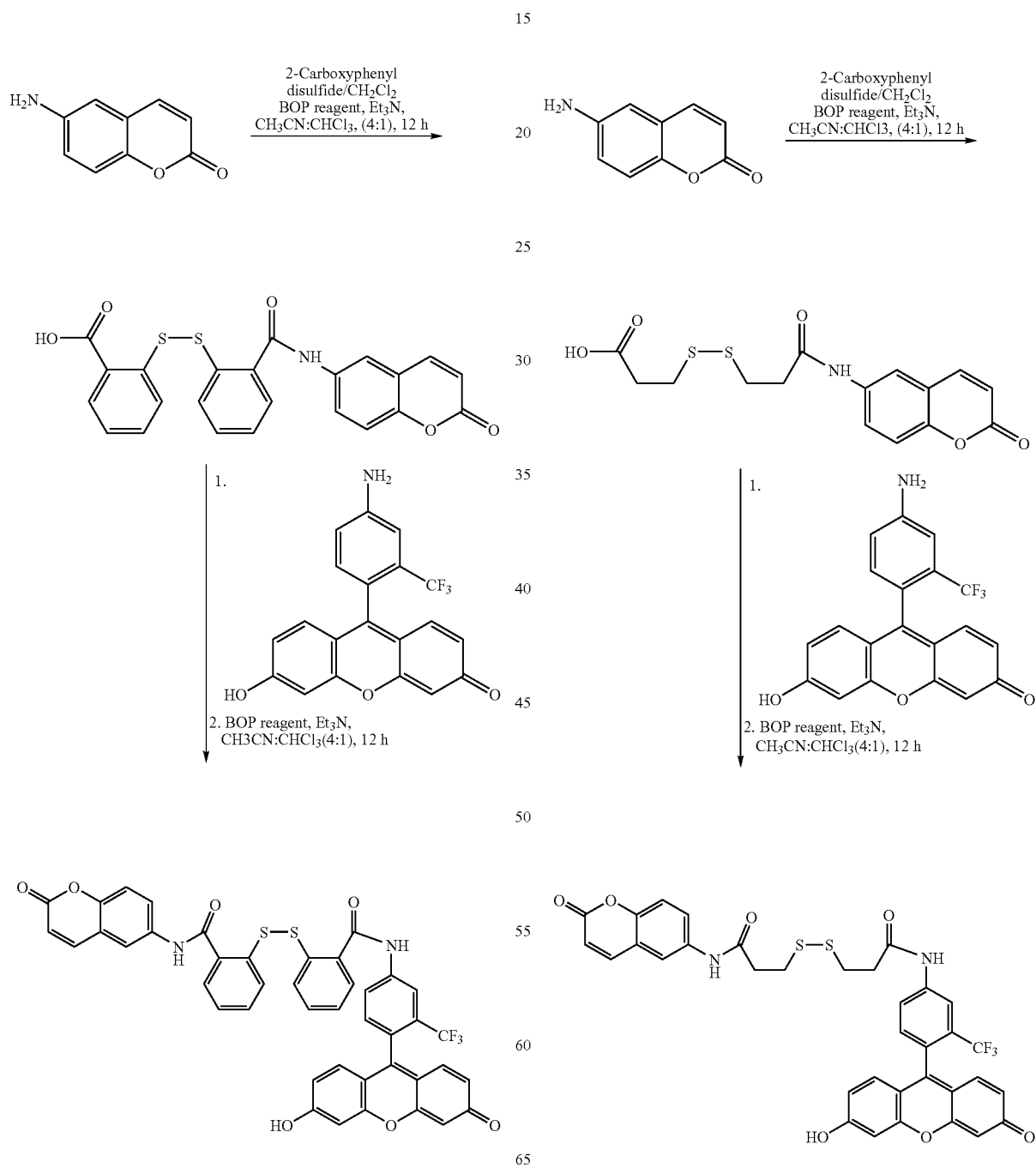

Example 19
Synthesis of 2-(6-Mercapto-3-thioxo-3H-thioxanthen-9-yl)-4-[4-(4-methyl-2-oxo-2H-chromen-7-yldisulfanyl)-thiobenzoylamino]-benzoic acid
The synthetic procedure described in Example 9 is modified in the scheme below:
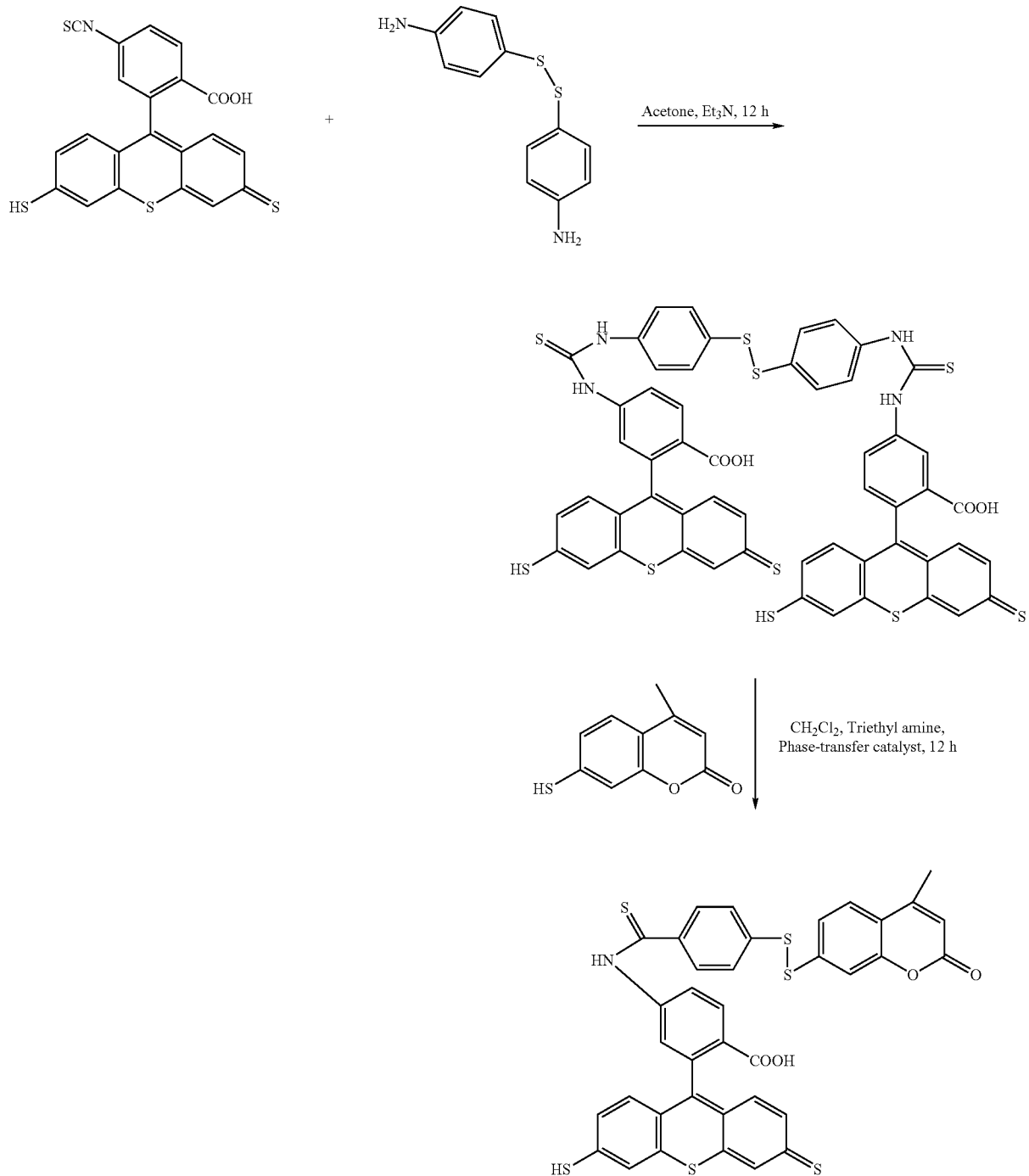

Example 20
Synthesis of {9-[2-(4-{3-[4-(4-{3-[4-Carboxy-3-(6-mercapto-3-thioxo-3H-thioxanthen-9-yl)-phenyl]-thioureido}-phenyldisulfanyl)-phenylcarbamoyl]-propionyl}-piperazine-1-carbonyl)-phenyl]-6-diethylamino-xanthen-3-ylidene}-diethyl-ammonium
The synthetic procedure described in Example 10 is modified in the scheme below:
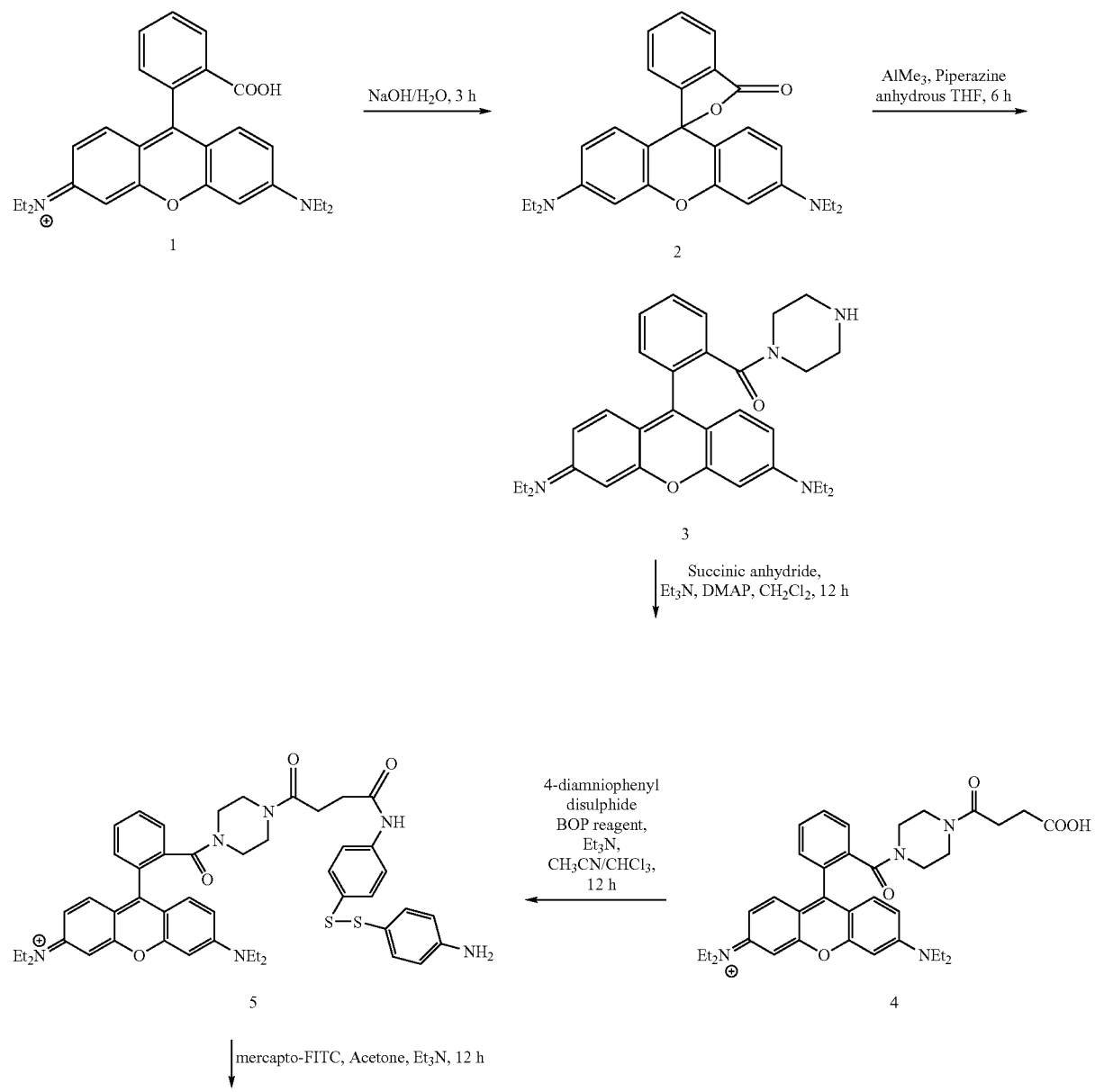

-continued
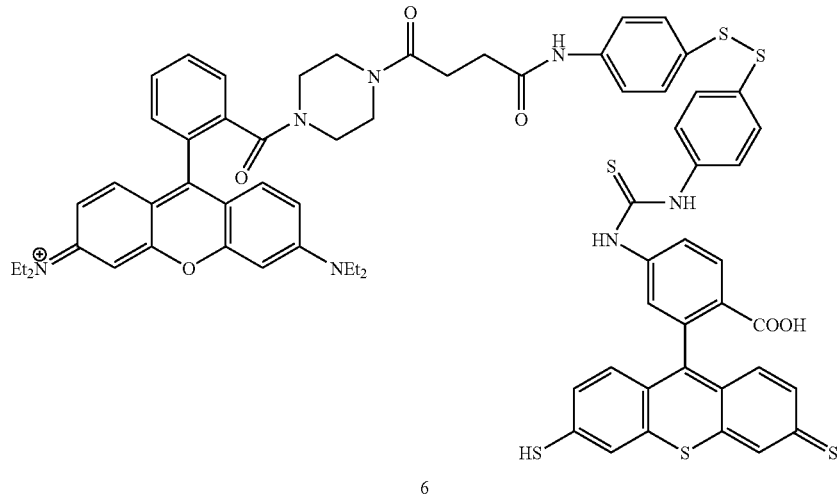
6
Structure of mercapto FTIC
25
Example 21
N-[4-(6-Mercapto-3-thioxo-3H-thioxanthen-9-yl)-3-trifluoromethyl-phenyl]-3-[2-(2-oxo-2H-chromen-6-ylcarbamoyl)-ethyldisulfanyl]-propionamide
The synthetic procedure described in Example 10 is modified in the scheme below.
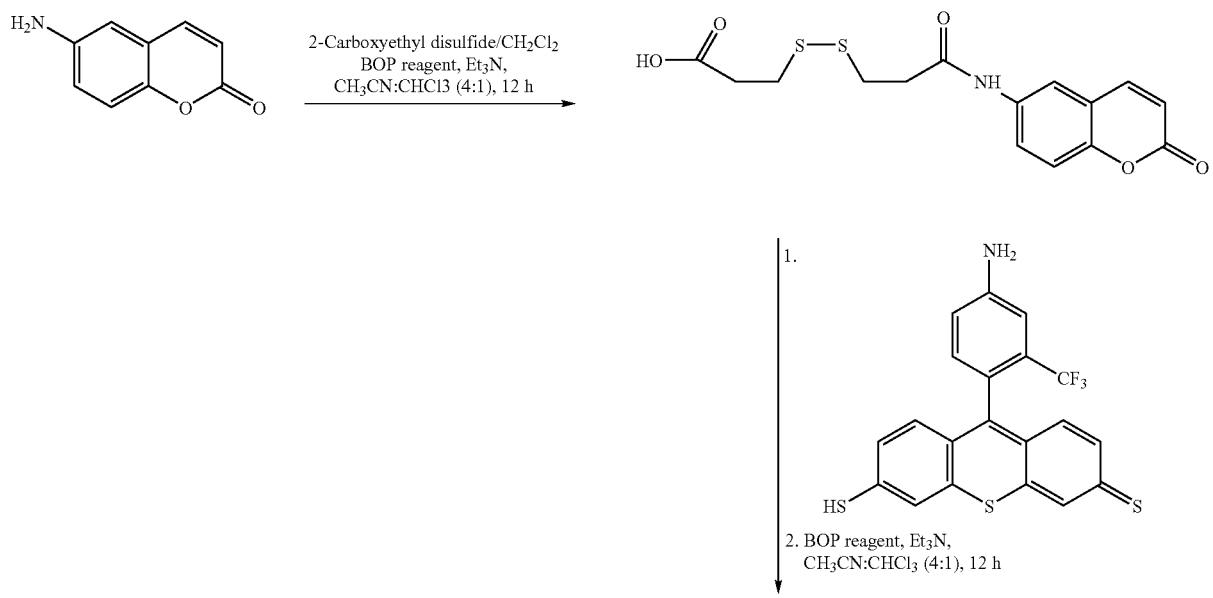

-continued
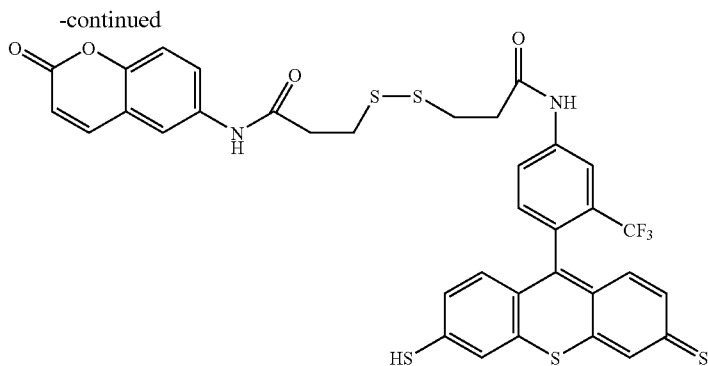
Example 22
(6-Diethylamino-9-{2-[4-(2-{2-[4-(6-mercapto-3-thioxo-3H-thioxanthen-9-yl)-3-trifluoromethyl-phenylcarbamoyl]-phenyldisulfanyl}-benzoyl)-piperazine-1-carbonyl]-phenyl}-xanthen-3-ylidene)-diethyl-ammonium
The synthetic procedure described in Example 10 is modified in the scheme below:
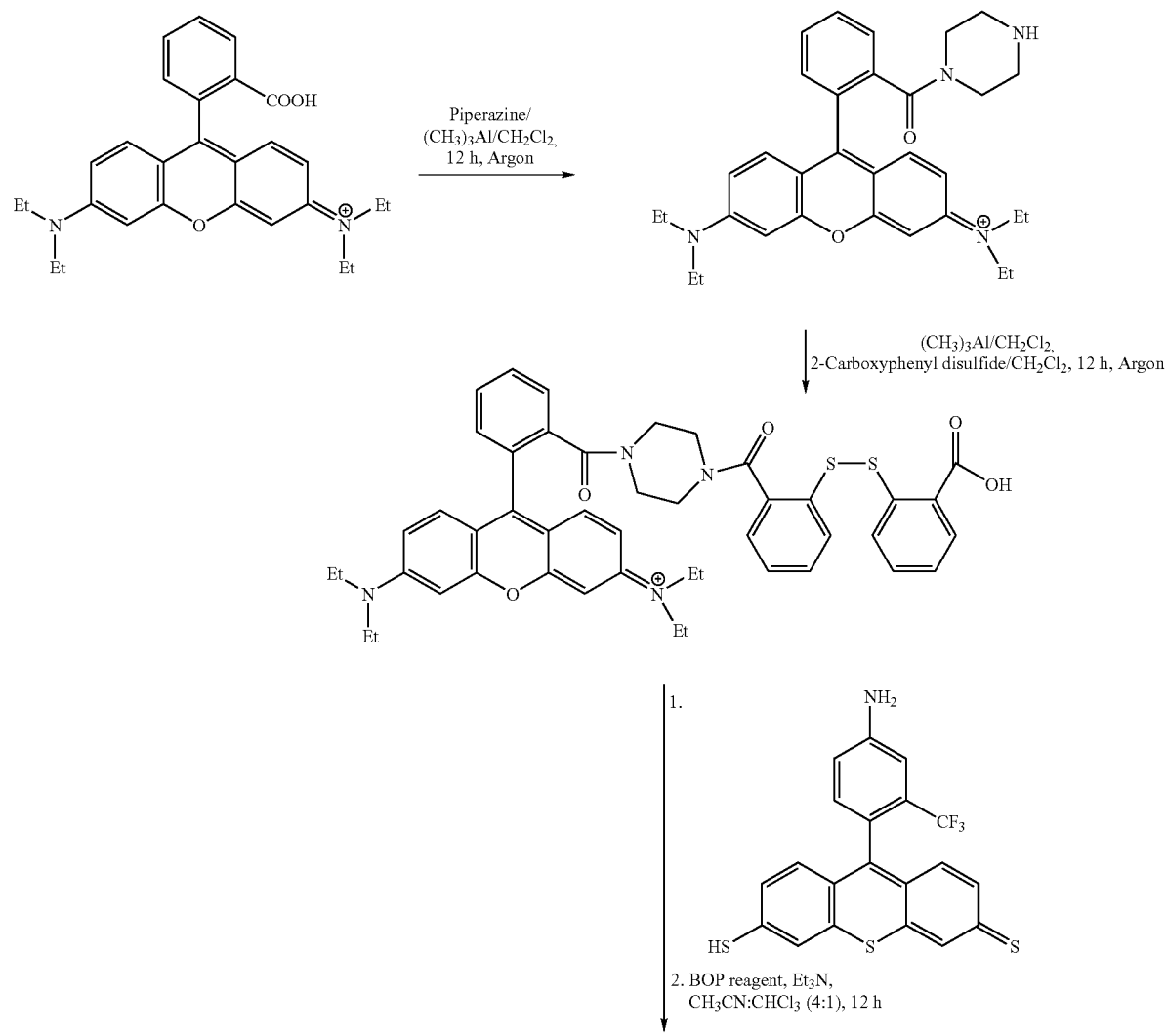

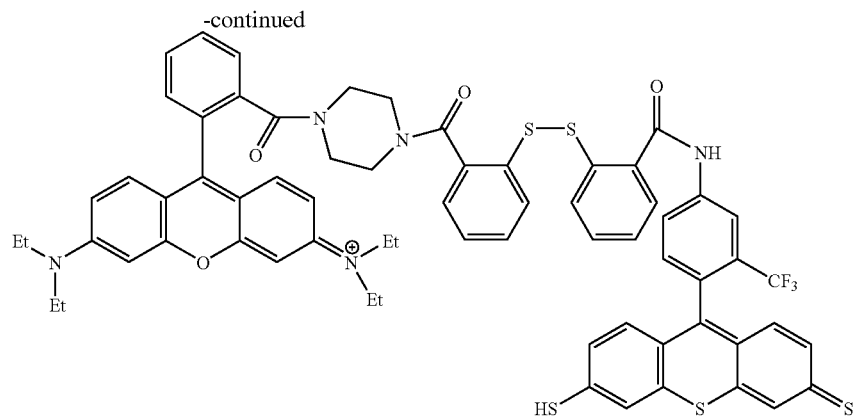

Example 23

FRET-Based Detection of Thiols

Hepes (pH 7.0) buffer was used in this study (FIG. 18) and fluorescence readings were made on a BMG Polarstar Galaxy fluorescence plate reader and/or on a Jasco FP-6500 spectrofluorometer. The experiment demonstrates the FRET capability of an $R^1$—S—S—$R^2$ probe (FIG. 18(a)). The probe (5 µM) was transferred to a 4 mL fluorescence cell and a three dimensional fluorescence spectra was recorded with excitation wavelength from 300 nm to 400 nm and emission wavelength from 400 nm to 600 nm. The coumarin chromophone has maximum excitation wavelength in the range of 310 to 325 nm and emits in the range of 400 nm to 425 nm. In FIG. 18(b), when coumarin-DAP-FITC was excited in the range of 300 to 330 nm, there is transfer of energy from coumarin to FITC (emission is only from FITC at 520 nm). The lack of emission from coumarin indicates that the FRET effect is efficient. When 5 µM coumarin DAP-FITC was treated with 1 mM DTT (FIG. 18(c)), there is an increase in coumarin emission (in the region of 400 to 425 nm), indicating the FRET donor/acceptor pair is broken at the disulphide bridge. This experiment clearly demonstrates the FRET capability of dithio probes. In conclusion, $R^1$—S—S—$R^2$ probes like coumarin-DAP-FITC demonstrate the FRET effect, and could be used to quantitate thiols both in vitro and in vivo. Analogues of this coumarin-DAP-FITC FRET pair can be used to tune excitation wavelengths in the range of 280 to 400 nm by placing different substitutions on the coumarin core. This includes using commercially available coumarin compounds and also coumarin compounds synthesized with functional groups like $NO_2$, CN, $NH_2$, COOH, CHO, alkyl, benzyl, pyridyl, naphthyl, indoles, etc at any of the synthetically feasible positions on benzyl ring of coumarin or lactone ring of coumarin. Accordingly, the functional properties of FITC or fluorescein can be changed by appropriate substitutions like $NO_2$, CN, $NH_2$, COOH, CHO, alkyl, benzyl, pyridyl, naphthyl, indoles, etc on any position of the two aromatic rings and also on the lactone ring. Coumarin-DAP-FITC analogues, like coumarin-DAP-Rhodamine 110, where in the coumarin is from the functionalized coumarin analogue, DAP is the functionalized diaminophenyl disulphide and rhodamine 110 is either commercially available rhodamine 110 or appropriately functionalized analogues of rhodamine 110.

Similar analogues of coumarin-DAP-FITC are described below and it should be noted that these are only a few representative examples and could include combinations of fluorescent probes available commercially or synthesized with appropriate substitutions on any of the probes or disulphide linkers. Examples include: coumarin-cystamine-rhodamine 110, coumarin-DAP-rhodamine 110, dansyl-cystamine-FITC, dansyl-DAP-FITC, dansyl-DAP-fluorescein, dansyl-cystamine-5-carboxy fluorescein, pyridyl-DAP-FITC, pyridyl-cystaminefluorescein, naphthyl-DAP-FITC, naphthyl-DAP-5-carboxy fluorescein, Bipyridyl-DAP-FITC, bipyridyl-cystamine-FITC, FITC-DAP-rhodamine B, fluorescien-cystamine-rhodamine B, Fluorescein-DAP-rhodamine B, Casade blue-DAP-chromomycin A3, Pyrene-DAP-dansyl, and Fast blue-DAP-FITC.

Dyes that can be used include the following commercially available dyes and their analogues, with appropriate substitution for linkage to any disulphide linker. A partial list dyes of which can be used for attaching on either side of disulphide linker, with the approximate excitation and emission maxima, are given in parenthesis and any appropriate combinations could be used to synthesize $R^1$—S—S—$R^2$ probes. Some of these probes are known by common names and where appropriate the IUPAC names of the probes are also given: Calcein blue (ex=375, em=420), cascade blue (400, 420), fast blue (365, 420), pyrene (345, 378), 4-methylumbelliferone (360, 449), 7-hydroxy-4-methyl coumarin (360, 449), 7-amino-4-methyl coumarin (351, 430), Pacific blue (410, 455), chromomycin A3 (450, 470), dansyl chlorie (380, 475), aniline blue (370, 509), 5-carboxy fluorescein (5FAM) (492, 518), dansyl cadavarine (335, 518), calcein (494, 517), eosin (524, 544), mathramycin (395, 535), rhodamine 110 (496, 520), rhodamine 123 (507, 529), rhodamine 6G (525, 555), erythrsin (529, 554), lissamine rhodamine B (570, 590), rhodamine B (555, 580), tetramethyl rhodamine (555, 580), 5-carboxy-X-rhodamine (574, 602), X-rhodamine (580, 605), 7-aminoactinomycin (546, 647), acridine orange (+RNA) (460, 650), ethidium homodimer1 (528, 617), phycocyanin (618, 642), 5-carboxynaphthofluorescein (598, 668), allophycocyanin (APC) (650, 660), APC-Cy5.5 (635, 660), APC-Cy7 (635, 767), 5-fluorescein isothiocyanate (494, 516), and fluorecein isothiocyanate (494, 516).

DAP and cystamine are representative classes of disulphide linkers. Other disulphide linkers will be analogues of these compounds, and include any disulphides with aromaric, aliphatic, heterocyclic, or bicyclic groups. The disulphide bridges can be homo- or hetero-substituted on either side of the disulphide bridge. Suitable disulphide linkers include homo and hetero disulphides synthesized by oxidation of a mixture of commercially available thiols.

Simple substitutions on aromatic and non aromatic rings of the dyes can include $NO_2$, CN, $NH_2$, COOH, CHO, alkyl, benzyl, pyridyl, naphthyl, and indoles.

Example 24

Use of $R^1$—S—S—$R^2$ Probes to Measure Reduction Potential

FRET (fluorescence resonance energy transfer) versions of the $R^1$—S—S—$R^2$ probes (called DSSA probes in this example) have been developed. Such probes permit excitation of the donor (at 490 nm for fluorescein, for example) and detection at the emission wavelength for an acceptor (at 600 nm for rhodamine, for example), possible because of energy transfer from donor to acceptor in the oxidized (S—S) probe. But, when probe is reduced (as in a fluorescein-S—S-rhodamine $R^1$—S—S—$R^2$ probe, for example), emission will only be observed for donor (at 520 nm for fluorescein), since energy transfer is no longer possible due to severing of the disulfide (S—S) bond. In this way, one can obtain the DS/DSSA ratio based on relative intensity of the emissions at 520 nm/600 nm, rather than by using absolute fluorescence values (not practical in vivo). A DS/DSSA ratio calculated from relative fluorescence values, along with $E^{o'}$, can then be used to calculate the ratio of reduced to oxidized thiols (CSH/CSSC), even in a living cell, using the Nernst equation. Another version of this type of probe is the coumarin/fluorescein donor acceptor pair (as in example 23). The probes reported here permit the first quantitative measurement of thiols in cells.

The fraction of probe (X) that is reduced after equilibration with a thiol reductant may be represented by the following equation:

$$X = 1-[DSSQ]/([DSSQ]+[DS])=1-(F_{max}-F_{max})/(F_{max}-F_0) \quad (1)$$

where Fmax is the fluorescence (Ex=490 nm, Em=520 nm) for fully reduced probe (DS), $F_0$ is the fluorescence for fully oxidized probe (DSSQ) and Fi is the fluorescence at some concentration of reductant. D is a donor and Q is a quencher. From X, an equilibrium constant for DSSQ reduction can be calculated according to the following:

$$K_{eq} = \frac{[CSSC][DS][QS]}{[CSH]^n[DSSQ]} = \frac{([DSSQ]_0(1-X))^3}{[DSSQ]_0(X)([CSH]_0 - n[DSSQ]_0(1-X))^n} \quad (2)$$

For a mono-thiol reductant like GSH (glutathione) and most proteins, n=2. CSH is the total concentration of thiol reductant (=protein-SH+GSH) in a reduced state, $[CSH]_0$ is its initial concentration and $[DSSQ]_0$ is initial concentration of dithio probe. These equations are for DSSQ, and require absolute fluorescence readings. If FRET probes are used (DSSA), then absolute fluorescence readings can be replaced by relative fluorescence emissions for Donor and Acceptor ($F^{Rel}=F_{Donor}/F_{Acceptor}$), which permits measurements of X and $K_{eq}$ in cells, because ratios for fully reduced or oxidized probes are independent of probe concentration (so in vitro-determined values of $F_{max}^{Rel}$ and $F_0^{Rel}$ can be used for in vivo calculations).

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

What is claimed is:

1. A dithio compound having a formula D-$X^1$—S—S—$X^2$-A, wherein D comprises a donor fluorophore; at least one of $X^1$ and $X^2$ comprises an aryl group; and A comprises an acceptor fluorophore that is different from the donor fluorophore and that is capable of at least one of:
   (A) quenching the donor fluorophore;
   (B) increasing or decreasing an extinction coefficient of the donor fluorophore; and
   (C) exhibiting sensitized emission when excited by the donor fluorophore.

2. The compound of claim 1, wherein the donor fluorophore has an absorbance maximum and the acceptor fluorophore has an absorbance maximum that differ by at least about 10 nm.

3. The compound of claim 1, wherein the donor fluorophore has an emission maximum and the acceptor fluorophore has an emission maximum that differ by at least about 10 nm.

4. The compound of claim 1, wherein the donor fluorophore has an emission spectrum and the acceptor fluorophore has an absorption spectrum, such that the emission spectrum and absorption spectrum overlap.

5. The compound of claim 4, wherein the emission spectrum and the absorption spectrum overlap by at least about 20%.

6. The compound of claim 1, wherein the acceptor fluorophore is capable of quenching the donor fluorophore by dynamic quenching.

7. The compound of claim 6, wherein the dynamic quenching occurs by fluorescence resonance energy transfer.

8. The compound of claim 1, wherein the acceptor fluorophore is capable of quenching the fluorophore by static quenching.

9. The compound of claim 1, wherein the sensitized emission includes fluorescence.

10. The compound of claim 1, wherein the sensitized emission occurs by fluorescence resonance energy transfer.

11. The compound of claim 1, wherein the donor fluorophore and the acceptor fluorophore are present in the compound at a distance of about 3-50 angstroms.

12. The compound of claim 1, wherein the donor fluorophore and the acceptor fluorophore are present in the compound at a distance of no more than about 20 angstroms.

13. The compound of claim 1, wherein the donor fluorophore comprises a xanthene-type fluorophore.

14. The compound of claim 1, wherein the acceptor fluorophore comprises a xanthene-type fluorophore.

15. A method for preparing the compound of claim 1 comprising reacting precursors that include:
   (A) a first precursor that comprises a donor fluorophore;
   (B) a second precursor that comprises an acceptor fluorophore; and
   (C) a dithio reagent having the formula $X^1$—S—S—$X^2$, wherein $X^1$ and $X^2$ may be the same or different and each comprise reactive groups capable of reacting with the first precursor and the second precursor.

16. The compound of claim 1, wherein both of $X^1$ and $X^2$ comprise an aryl group.

17. The compound of claim 1, wherein the aryl group is substituted with an amide group.

18. The compound of claim 17, wherein at least one of $X^1$ and $X^2$ comprise an aryl group substituted with an amide group and having a formula selected from:

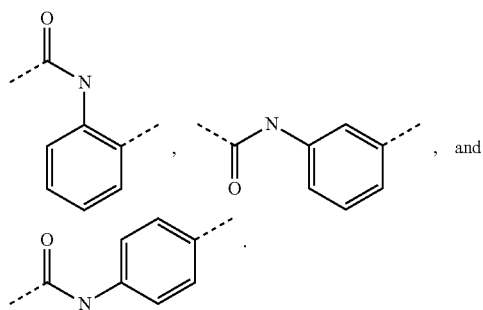

19. The compound of claim 18, wherein both of $X^1$ and $X^2$ comprise an aryl group substituted with an amide group and having a formula selected from:

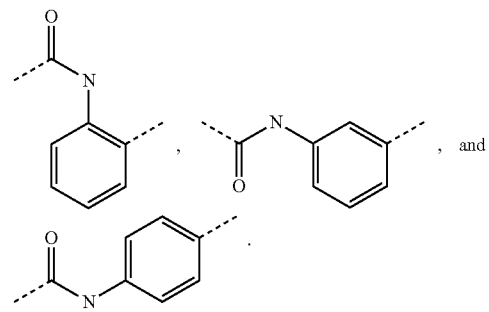

20. The compound of claim 19, wherein the dithio compound has a formula:

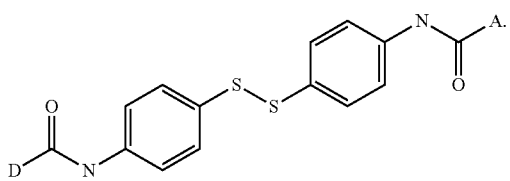

21. The compound of claim 1, wherein the donor fluorophore is selected from a group consisting of fluorescein and Alexa488 and the acceptor fluorophore is selected from a group consisting of para-methyl red and rhodamine.

22. The compound of claim 1, wherein the donor fluorophore is coumarin and the acceptor fluorophore is fluorescein.

23. The method of claim 15, wherein the dithio reagent is a diaminodiphenyldisulfide reagent.

24. The method of claim 23, wherein the diaminodiphenyldisulfide reagent is p,p'-diaminodiphenyldisulfide.

25. A dithio compound having a formula D-S—S-A, wherein D comprises coumarin and A comprises fluorescein.